United States Patent
Taber et al.

(10) Patent No.: US 9,724,136 B2
(45) Date of Patent: Aug. 8, 2017

(54) SPINOUS PROCESS IMPLANTS AND ASSOCIATED METHODS

(71) Applicant: Zimmer Biomet Spine, Inc., Broomfield, CO (US)

(72) Inventors: Justin Taber, Lafayette, CO (US); Andrew Lamborne, Golden, CO (US); Michael Fulton, Superior, CO (US); Jeffrey J Thramann, Longmont, CO (US)

(73) Assignee: Zimmer Biomet Spine, Inc., Broomfield, CO (US)

( * ) Notice: Subject to any disclaimer, the term of this patent is extended or adjusted under 35 U.S.C. 154(b) by 0 days.

(21) Appl. No.: 14/980,982

(22) Filed: Dec. 28, 2015

(65) Prior Publication Data

US 2016/0113687 A1    Apr. 28, 2016

Related U.S. Application Data

(63) Continuation of application No. 12/751,856, filed on Mar. 31, 2010, now Pat. No. 9,247,968, which is a
(Continued)

(51) Int. Cl.
*A61B 17/70* (2006.01)
*A61B 17/84* (2006.01)
*A61B 17/00* (2006.01)

(52) U.S. Cl.
CPC ...... *A61B 17/7071* (2013.01); *A61B 17/7053* (2013.01); *A61B 17/7061* (2013.01);
(Continued)

(58) Field of Classification Search
USPC .................................................. 606/248–249
See application file for complete search history.

(56) References Cited

U.S. PATENT DOCUMENTS

| 84,815 A | 12/1868 | Garvin |
|---|---|---|
| 242,443 A | 6/1881 | Foote |

(Continued)

FOREIGN PATENT DOCUMENTS

| CN | 101129271 A | 2/2008 |
|---|---|---|
| EP | 1266606 A2 | 12/2002 |

(Continued)

OTHER PUBLICATIONS

"U.S. Appl. No. 11/934,604, Applicant's Summary of Examiner Interview filed Sep. 12, 2011", 1 pgs.
(Continued)

*Primary Examiner* — Jan Christopher Merene
(74) *Attorney, Agent, or Firm* — Schwegman Lundberg & Woessner, P.A.

(57) ABSTRACT

The present invention provides spinous process implant and associated methods. In one aspect of the invention the implant limits the maximum spacing between the spinous processes. In another aspect of the invention, a spacer has at least one transverse opening to facilitate tissue in-growth. In another aspect of the invention, an implant includes a spacer and separate extensions engageable with the spacer. In another aspect of the invention, instrumentation for inserting the implant is provided. In other aspects of the invention, methods for treating spine disease are provided.

17 Claims, 26 Drawing Sheets

Related U.S. Application Data continuation-in-part of application No. 11/934,604, filed on Nov. 2, 2007, now Pat. No. 8,241,330.

(60) Provisional application No. 60/912,273, filed on Apr. 17, 2007, provisional application No. 60/884,581, filed on Jan. 11, 2007, provisional application No. 61/165,354, filed on Mar. 31, 2009.

(52) U.S. Cl.
CPC ........ *A61B 17/7068* (2013.01); *A61B 17/842* (2013.01); *A61B 2017/00477* (2013.01)

(56) References Cited

U.S. PATENT DOCUMENTS

| | | |
|---|---|---|
| 465,161 A | 12/1891 | Chase |
| 765,879 A | 7/1904 | Campbell |
| 832,201 A | 10/1906 | Kistler |
| 1,137,585 A | 4/1915 | Craig, Jr. |
| 1,331,737 A | 2/1920 | Ylisto |
| 1,400,648 A | 12/1921 | Whitney |
| 1,725,670 A | 8/1929 | Novack |
| 1,737,488 A | 11/1929 | Zohlen |
| 2,137,121 A | 11/1938 | Greenwald |
| 2,677,369 A | 5/1954 | Knowles |
| 2,689,568 A | 9/1954 | Wakefield |
| 2,774,350 A | 12/1956 | Cleveland, Jr. |
| 2,789,860 A | 4/1957 | Knowles |
| 3,025,853 A | 3/1962 | Mason |
| 3,039,468 A | 6/1962 | Price |
| 3,242,922 A | 3/1966 | Thomas |
| 3,409,013 A | 11/1968 | Berry |
| 3,628,535 A | 12/1971 | Ostrowsky et al. |
| 3,648,691 A | 3/1972 | Lumb et al. |
| 3,648,961 A | 3/1972 | Farrow |
| 3,788,318 A | 1/1974 | Kim et al. |
| 3,789,852 A | 2/1974 | Kim et al. |
| 4,092,788 A | 6/1978 | Gowing |
| 4,269,178 A | 5/1981 | Keene |
| 4,274,401 A | 6/1981 | Miskew |
| 4,369,769 A | 1/1983 | Edwards |
| 4,369,770 A | 1/1983 | Bacal et al. |
| 4,409,968 A | 10/1983 | Drummond |
| 4,448,191 A | 5/1984 | Rodnyansky et al. |
| 4,554,914 A | 11/1985 | Kapp et al. |
| 4,570,618 A | 2/1986 | Wu |
| 4,573,454 A | 3/1986 | Hoffman |
| 4,599,086 A | 7/1986 | Doty |
| 4,636,217 A | 1/1987 | Ogilvie et al. |
| 4,697,582 A | 10/1987 | William |
| 4,773,402 A | 9/1988 | Asher et al. |
| 4,892,545 A | 1/1990 | Day et al. |
| 5,007,909 A | 4/1991 | Rogozinski |
| 5,010,879 A | 4/1991 | Moriya et al. |
| 5,011,484 A | 4/1991 | Breard |
| 5,030,220 A | 7/1991 | Howland |
| 5,062,850 A | 11/1991 | Macmillan et al. |
| 5,306,275 A | 4/1994 | Bryan |
| 5,390,683 A | 2/1995 | Pisharodi |
| 5,413,576 A | 5/1995 | Rivard |
| 5,472,426 A | 12/1995 | Bonati et al. |
| 5,496,318 A | 3/1996 | Howland et al. |
| 5,503,617 A | 4/1996 | Jako |
| 5,527,312 A | 6/1996 | Ray |
| 5,540,703 A | 7/1996 | Barker, Jr. et al. |
| 5,609,634 A | 3/1997 | Voydeville |
| 5,609,636 A | 3/1997 | Kohrs et al. |
| 5,628,756 A | 5/1997 | Barker, Jr. et al. |
| 5,645,599 A | 7/1997 | Samani |
| 5,653,763 A | 8/1997 | Errico et al. |
| 5,658,335 A | 8/1997 | Allen |
| 5,702,452 A | 12/1997 | Argenson et al. |
| 5,702,453 A | 12/1997 | Rabbe et al. |
| 5,716,358 A | 2/1998 | Ochoa et al. |
| 5,725,582 A | 3/1998 | Bevan et al. |
| 5,800,550 A | 9/1998 | Sertich |
| 5,813,978 A | 9/1998 | Jako |
| 5,836,948 A | 11/1998 | Zucherman et al. |
| 5,860,977 A | 1/1999 | Zucherman et al. |
| 5,876,404 A | 3/1999 | Zucherman et al. |
| 5,928,232 A | 7/1999 | Howland et al. |
| 5,989,256 A | 11/1999 | Kuslich et al. |
| 6,045,442 A | 4/2000 | Bounds |
| 6,045,552 A | 4/2000 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,099,527 A | 8/2000 | Hochschuler et al. |
| 6,102,950 A | 8/2000 | Vaccaro |
| 6,132,464 A | 10/2000 | Martin |
| 6,149,652 A | 11/2000 | Zucherman et al. |
| 6,152,926 A | 11/2000 | Zucherman et al. |
| 6,156,038 A | 12/2000 | Zucherman |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,200,322 B1 | 3/2001 | Branch et al. |
| 6,231,610 B1 | 5/2001 | Geisler |
| 6,235,030 B1 | 5/2001 | Zucherman et al. |
| 6,235,059 B1 | 5/2001 | Benezech et al. |
| 6,238,397 B1 | 5/2001 | Zucherman et al. |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,340,362 B1 | 1/2002 | Pierer et al. |
| 6,364,883 B1 | 4/2002 | Santilli |
| 6,375,682 B1 | 4/2002 | Fleischmann et al. |
| 6,379,355 B1 | 4/2002 | Zucherman et al. |
| 6,398,811 B1 | 6/2002 | Mckay |
| 6,416,776 B1 | 7/2002 | Shamie |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,478,796 B2 | 11/2002 | Zucherman et al. |
| 6,500,178 B2 | 12/2002 | Zucherman et al. |
| 6,514,255 B1 | 2/2003 | Ferree |
| 6,514,256 B2 | 2/2003 | Zucherman et al. |
| 6,520,907 B1 | 2/2003 | Foley et al. |
| 6,582,433 B2 | 6/2003 | Yun |
| 6,589,243 B1 | 7/2003 | Viart et al. |
| 6,599,294 B2 | 7/2003 | Fuss et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,656,185 B2 | 12/2003 | Gleason et al. |
| 6,669,729 B2 | 12/2003 | Chin |
| 6,679,833 B2 | 1/2004 | Smith et al. |
| 6,682,563 B2 | 1/2004 | Scharf |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman et al. |
| 6,746,485 B1 | 6/2004 | Zucherman et al. |
| 6,761,720 B1 | 7/2004 | Senegas |
| 6,796,983 B1 | 9/2004 | Zucherman et al. |
| 6,800,084 B2 | 10/2004 | Davison et al. |
| 6,835,205 B2 | 12/2004 | Atkinson et al. |
| 6,902,566 B2 | 6/2005 | Zucherman et al. |
| 6,902,580 B2 | 6/2005 | Fallin et al. |
| 6,926,728 B2 | 8/2005 | Zucherman et al. |
| 6,946,000 B2 | 9/2005 | Senegas et al. |
| 6,966,929 B2 | 11/2005 | Mitchell |
| 6,989,011 B2 | 1/2006 | Paul et al. |
| 7,029,473 B2 | 4/2006 | Zucherman et al. |
| 7,048,736 B2 | 5/2006 | Robinson et al. |
| 7,083,649 B2 | 8/2006 | Zucherman et al. |
| 7,087,083 B2 | 8/2006 | Pasquet et al. |

(56) References Cited

U.S. PATENT DOCUMENTS

| | | |
|---|---|---|
| 7,101,375 B2 | 9/2006 | Zucherman et al. |
| 7,131,972 B2 | 11/2006 | Mazda et al. |
| 7,163,558 B2 | 1/2007 | Senegas et al. |
| 7,189,234 B2 | 3/2007 | Zucherman et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,442,208 B2 | 10/2008 | Mathieu et al. |
| 7,458,981 B2 | 12/2008 | Fielding et al. |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,510,567 B2 | 3/2009 | Zucherman et al. |
| 7,520,887 B2 | 4/2009 | Maxy et al. |
| 7,530,991 B2 | 5/2009 | Nekozuka et al. |
| 7,537,613 B2 | 5/2009 | Arnin et al. |
| 7,549,999 B2 | 6/2009 | Zucherman et al. |
| 7,585,313 B2 | 9/2009 | Kwak et al. |
| 7,585,316 B2 | 9/2009 | Trieu |
| 7,588,592 B2 | 9/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,912 B2 | 12/2009 | Iwasaki et al. |
| 7,658,752 B2 | 2/2010 | Labrom et al. |
| 7,753,938 B2 | 7/2010 | Aschmann et al. |
| 7,799,058 B2 | 9/2010 | Froehlich et al. |
| 7,871,426 B2 | 1/2011 | Chin et al. |
| 7,918,875 B2 | 4/2011 | Lins et al. |
| 7,922,750 B2 | 4/2011 | Trautwein et al. |
| 7,955,392 B2 | 6/2011 | Dewey et al. |
| 7,959,652 B2 | 6/2011 | Zucherman et al. |
| 8,007,517 B2 | 8/2011 | Lins et al. |
| 8,012,207 B2 | 9/2011 | Kim |
| 8,048,120 B1 * | 11/2011 | Fallin ............... A61B 17/7068 606/246 |
| 8,075,593 B2 | 12/2011 | Hess |
| 8,105,382 B2 | 1/2012 | Olmos et al. |
| 8,167,915 B2 | 5/2012 | Ferree et al. |
| 8,241,330 B2 | 8/2012 | Lamborne et al. |
| 8,382,801 B2 | 2/2013 | Lamborne et al. |
| 8,403,959 B2 | 3/2013 | Döllinger |
| 9,055,981 B2 | 6/2015 | Lamborne et al. |
| 9,247,968 B2 | 2/2016 | Taber et al. |
| 9,265,532 B2 | 2/2016 | Lamborne et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0016776 A1 | 8/2001 | Zuckerman et al. |
| 2001/0020170 A1 | 9/2001 | Zucherman et al. |
| 2001/0021850 A1 | 9/2001 | Zucherman |
| 2001/0021851 A1 | 9/2001 | Eberlein et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0029081 A1 | 3/2002 | Scarborough et al. |
| 2002/0045899 A1 | 4/2002 | Errico et al. |
| 2002/0095154 A1 | 7/2002 | Atkinson et al. |
| 2002/0116000 A1 | 8/2002 | Zucherman et al. |
| 2002/0143331 A1 | 10/2002 | Zucherman et al. |
| 2002/0183746 A1 | 12/2002 | Zucherman et al. |
| 2003/0040746 A1 | 2/2003 | Mitchell et al. |
| 2003/0045935 A1 | 3/2003 | Angelucci et al. |
| 2003/0065330 A1 | 4/2003 | Zucherman et al. |
| 2003/0065396 A1 | 4/2003 | Michelson |
| 2003/0083688 A1 | 5/2003 | Simonson |
| 2003/0139812 A1 | 7/2003 | Garcia et al. |
| 2003/0153912 A1 | 8/2003 | Graf |
| 2003/0153915 A1 | 8/2003 | Nekozuka et al. |
| 2003/0216736 A1 | 11/2003 | Robinson et al. |
| 2003/0220643 A1 | 11/2003 | Ferree |
| 2004/0024458 A1 | 2/2004 | Senegas et al. |
| 2004/0059339 A1 | 3/2004 | Roehm, III et al. |
| 2004/0093001 A1 | 5/2004 | Hamada |
| 2004/0097931 A1 | 5/2004 | Mitchell |
| 2004/0106995 A1 | 6/2004 | Le Couedic et al. |
| 2004/0119121 A1 | 6/2004 | Kariyazono |
| 2004/0138749 A1 | 7/2004 | Zucherman et al. |
| 2004/0138750 A1 | 7/2004 | Mitchell |
| 2004/0143270 A1 | 7/2004 | Zucherman et al. |
| 2004/0147937 A1 | 7/2004 | Dunbar et al. |
| 2004/0153071 A1 | 8/2004 | Zucherman et al. |
| 2004/0162617 A1 | 8/2004 | Zucherman et al. |
| 2004/0167520 A1 | 8/2004 | Zucherman et al. |
| 2004/0167521 A1 | 8/2004 | De Windt |
| 2004/0172135 A1 | 9/2004 | Mitchell |
| 2004/0181282 A1 | 9/2004 | Zucherman et al. |
| 2004/0193159 A1 | 9/2004 | Zucherman et al. |
| 2004/0199168 A1 | 10/2004 | Bertagnoli et al. |
| 2004/0220568 A1 | 11/2004 | Zucherman et al. |
| 2004/0249379 A1 | 12/2004 | Winslow et al. |
| 2005/0010293 A1 | 1/2005 | Zucherman et al. |
| 2005/0010296 A1 | 1/2005 | Mitchell |
| 2005/0010298 A1 | 1/2005 | Zucherman et al. |
| 2005/0075634 A1 | 4/2005 | Zucherman et al. |
| 2005/0085855 A1 | 4/2005 | Forsberg |
| 2005/0101955 A1 | 5/2005 | Zucherman et al. |
| 2005/0113926 A1 | 5/2005 | Zucherman et al. |
| 2005/0125065 A1 | 6/2005 | Zucherman et al. |
| 2005/0143738 A1 | 6/2005 | Zucherman et al. |
| 2005/0143740 A1 | 6/2005 | Morris et al. |
| 2005/0143820 A1 | 6/2005 | Zucherman et al. |
| 2005/0143826 A1 | 6/2005 | Zucherman et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0149196 A1 | 7/2005 | Zucherman et al. |
| 2005/0154462 A1 | 7/2005 | Zucherman et al. |
| 2005/0165398 A1 | 7/2005 | Reiley |
| 2005/0192574 A1 | 9/2005 | Blain |
| 2005/0192586 A1 | 9/2005 | Zucherman et al. |
| 2005/0196420 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0234452 A1 | 10/2005 | Malandain |
| 2005/0240182 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2005/0283237 A1 | 12/2005 | Zucherman et al. |
| 2005/0283242 A1 | 12/2005 | Zucherman et al. |
| 2005/0283243 A1 | 12/2005 | Zucherman et al. |
| 2005/0288672 A1 | 12/2005 | Ferree |
| 2006/0004447 A1 | 1/2006 | Mastrorio et al. |
| 2006/0015099 A1 | 1/2006 | Cannon et al. |
| 2006/0015181 A1 | 1/2006 | Elberg |
| 2006/0036246 A1 | 2/2006 | Carl et al. |
| 2006/0036258 A1 | 2/2006 | Zucherman et al. |
| 2006/0036259 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0084983 A1 | 4/2006 | Kim |
| 2006/0084985 A1 | 4/2006 | Kim |
| 2006/0084988 A1 | 4/2006 | Kim |
| 2006/0084994 A1 | 4/2006 | Atkinson et al. |
| 2006/0085069 A1 | 4/2006 | Kim et al. |
| 2006/0085070 A1 | 4/2006 | Kim |
| 2006/0089654 A1 | 4/2006 | Lins et al. |
| 2006/0089718 A1 | 4/2006 | Zucherman et al. |
| 2006/0106361 A1 | 5/2006 | Muni et al. |
| 2006/0106381 A1 | 5/2006 | Ferree et al. |
| 2006/0106397 A1 | 5/2006 | Lins et al. |
| 2006/0122606 A1 | 6/2006 | Wolgen |
| 2006/0122620 A1 | 6/2006 | Kim |
| 2006/0124247 A1 | 6/2006 | Collins et al. |
| 2006/0136060 A1 | 6/2006 | Taylor |
| 2006/0142761 A1 | 6/2006 | Landry et al. |

(56) References Cited

U.S. PATENT DOCUMENTS

| | | |
|---|---|---|
| 2006/0161154 A1 | 7/2006 | Mcafee |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235400 A1 | 10/2006 | Schneider |
| 2006/0235409 A1 | 10/2006 | Blain |
| 2006/0235521 A1 | 10/2006 | Zucherman et al. |
| 2006/0235533 A1 | 10/2006 | Blain |
| 2006/0241601 A1 | 10/2006 | Trautwein et al. |
| 2006/0241610 A1 | 10/2006 | Lim et al. |
| 2006/0241757 A1 | 10/2006 | Anderson |
| 2006/0247623 A1 | 11/2006 | Anderson |
| 2006/0247634 A1 | 11/2006 | Warner et al. |
| 2006/0247640 A1 | 11/2006 | Blackwell et al. |
| 2006/0259037 A1 | 11/2006 | Hartmann et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271055 A1 | 11/2006 | Thramann |
| 2006/0271194 A1 | 11/2006 | Zucherman et al. |
| 2006/0282079 A1 | 12/2006 | Labrom et al. |
| 2006/0293662 A1 | 12/2006 | Boyer, II et al. |
| 2007/0005064 A1 | 1/2007 | Anderson et al. |
| 2007/0010813 A1 | 1/2007 | Zucherman et al. |
| 2007/0016303 A1 | 1/2007 | Jackson |
| 2007/0032790 A1 | 2/2007 | Aschmann et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049934 A1 | 3/2007 | Edidin et al. |
| 2007/0049935 A1 | 3/2007 | Edidin et al. |
| 2007/0049943 A1 | 3/2007 | Moskowitz et al. |
| 2007/0055237 A1 | 3/2007 | Edidin et al. |
| 2007/0055246 A1 | 3/2007 | Zucherman et al. |
| 2007/0055276 A1 | 3/2007 | Edidin |
| 2007/0073292 A1 | 3/2007 | Kohm et al. |
| 2007/0093823 A1 | 4/2007 | Booth et al. |
| 2007/0093825 A1 | 4/2007 | Ferree et al. |
| 2007/0093828 A1 | 4/2007 | Abdou |
| 2007/0093830 A1 | 4/2007 | Zucherman et al. |
| 2007/0100340 A1 | 5/2007 | Lange et al. |
| 2007/0106298 A1 | 5/2007 | Carli et al. |
| 2007/0106385 A1 | 5/2007 | Zucherman et al. |
| 2007/0118120 A1 | 5/2007 | Stevenson et al. |
| 2007/0123861 A1 | 5/2007 | Dewey et al. |
| 2007/0142915 A1 | 6/2007 | Altarac et al. |
| 2007/0149972 A1 | 6/2007 | Nakajima et al. |
| 2007/0152001 A1 | 7/2007 | Cho et al. |
| 2007/0161993 A1 | 7/2007 | Lowery et al. |
| 2007/0162000 A1 | 7/2007 | Perkins |
| 2007/0162005 A1 | 7/2007 | Peterson et al. |
| 2007/0167945 A1 | 7/2007 | Lange et al. |
| 2007/0173818 A1 | 7/2007 | Hestad et al. |
| 2007/0173821 A1 | 7/2007 | Trieu |
| 2007/0173823 A1 | 7/2007 | Dewey et al. |
| 2007/0173832 A1 | 7/2007 | Tebbe et al. |
| 2007/0179500 A1 | 8/2007 | Chin et al. |
| 2007/0185490 A1 | 8/2007 | Implicito |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0191847 A1 | 8/2007 | Arnin et al. |
| 2007/0191947 A1 | 8/2007 | Arnin et al. |
| 2007/0191948 A1 | 8/2007 | Arnin et al. |
| 2007/0191949 A1 | 8/2007 | Arnin et al. |
| 2007/0191950 A1 | 8/2007 | Arnin et al. |
| 2007/0203490 A1 | 8/2007 | Zucherman et al. |
| 2007/0203491 A1 | 8/2007 | Pasquet et al. |
| 2007/0203493 A1 | 8/2007 | Zucherman et al. |
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208347 A1 | 9/2007 | Zucherman et al. |
| 2007/0213724 A1 | 9/2007 | Arnin et al. |
| 2007/0213829 A1 | 9/2007 | Le Couedic et al. |
| 2007/0219552 A1 | 9/2007 | Zucherman et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233088 A1 | 10/2007 | Edmond |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain |
| 2007/0265624 A1 | 11/2007 | Zucherman et al. |
| 2007/0265625 A1 | 11/2007 | Zucherman et al. |
| 2007/0270812 A1 | 11/2007 | Peckham |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0270968 A1 | 11/2007 | Baynham et al. |
| 2007/0272259 A1 | 11/2007 | Allard et al. |
| 2007/0276368 A1 | 11/2007 | Trieu et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276381 A1 | 11/2007 | Butler et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2007/0282340 A1 | 12/2007 | Malandain |
| 2007/0282442 A1 | 12/2007 | Malandain et al. |
| 2007/0282443 A1 | 12/2007 | Globerman et al. |
| 2007/0288006 A1 | 12/2007 | Arnin et al. |
| 2007/0299526 A1 | 12/2007 | Malandain |
| 2008/0004706 A1 | 1/2008 | Arnin et al. |
| 2008/0009947 A1 | 1/2008 | Arnin et al. |
| 2008/0009948 A1 | 1/2008 | Arnin et al. |
| 2008/0015693 A1 | 1/2008 | Le Couedic |
| 2008/0015700 A1 | 1/2008 | Zucherman et al. |
| 2008/0015809 A1 | 1/2008 | Alumbaugh et al. |
| 2008/0021460 A1 | 1/2008 | Bruneau et al. |
| 2008/0021471 A1 | 1/2008 | Winslow et al. |
| 2008/0021488 A1 | 1/2008 | Berberich |
| 2008/0021560 A1 | 1/2008 | Zucherman et al. |
| 2008/0021561 A1 | 1/2008 | Zucherman et al. |
| 2008/0027433 A1 | 1/2008 | Kohm et al. |
| 2008/0027434 A1 | 1/2008 | Zucherman et al. |
| 2008/0027435 A1 | 1/2008 | Zucherman et al. |
| 2008/0027438 A1 | 1/2008 | Abdou |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033552 A1 | 2/2008 | Lee et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039853 A1 | 2/2008 | Zucherman et al. |

(56) References Cited

U.S. PATENT DOCUMENTS

| | | |
|---|---|---|
| 2008/0039858 A1 | 2/2008 | Zucherman et al. |
| 2008/0039859 A1 | 2/2008 | Zucherman et al. |
| 2008/0039944 A1 | 2/2008 | Malandain et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051891 A1 | 2/2008 | Malandain et al. |
| 2008/0051892 A1 | 2/2008 | Malandain et al. |
| 2008/0051893 A1 | 2/2008 | Malandain et al. |
| 2008/0051894 A1 | 2/2008 | Malandain et al. |
| 2008/0051895 A1 | 2/2008 | Malandain et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0051906 A1 | 2/2008 | Malandain et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058934 A1 | 3/2008 | Malandain et al. |
| 2008/0058935 A1 | 3/2008 | Malandain et al. |
| 2008/0058936 A1 | 3/2008 | Malandain et al. |
| 2008/0058937 A1 | 3/2008 | Malandain et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071376 A1 | 3/2008 | Kohm et al. |
| 2008/0071378 A1 | 3/2008 | Zucherman et al. |
| 2008/0071380 A1 | 3/2008 | Sweeney |
| 2008/0082118 A1 | 4/2008 | Edidin et al. |
| 2008/0082167 A1 | 4/2008 | Edidin et al. |
| 2008/0082172 A1 | 4/2008 | Jackson |
| 2008/0086212 A1 | 4/2008 | Zucherman et al. |
| 2008/0108990 A1 | 5/2008 | Mitchell et al. |
| 2008/0109082 A1 | 5/2008 | Fink et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0132952 A1 | 6/2008 | Malandain et al. |
| 2008/0140125 A1 | 6/2008 | Mitchell et al. |
| 2008/0140207 A1 | 6/2008 | Olmos et al. |
| 2008/0147190 A1 | 6/2008 | Dewey et al. |
| 2008/0147192 A1 | 6/2008 | Edidin et al. |
| 2008/0161822 A1 | 7/2008 | Perez-Cruet et al. |
| 2008/0161856 A1 | 7/2008 | Liu et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177271 A1 | 7/2008 | Yeh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0183210 A1 | 7/2008 | Zucherman et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234733 A1 | 9/2008 | Scrantz et al. |
| 2008/0234735 A1 | 9/2008 | Joshi |
| 2008/0234824 A1 | 9/2008 | Youssef et al. |
| 2008/0243186 A1 | 10/2008 | Abdou |
| 2008/0243250 A1 | 10/2008 | Seifert et al. |
| 2008/0249528 A1 | 10/2008 | Khalife et al. |
| 2008/0249569 A1 | 10/2008 | Waugh et al. |
| 2008/0249622 A1 | 10/2008 | Gray |
| 2008/0255616 A1 | 10/2008 | Atkinson et al. |
| 2008/0255668 A1 | 10/2008 | Fallin et al. |
| 2008/0255669 A1 | 10/2008 | Fallin et al. |
| 2008/0262617 A1 | 10/2008 | Froehlich et al. |
| 2008/0262619 A1 | 10/2008 | Ray |
| 2008/0269904 A1 | 10/2008 | Voorhies |
| 2008/0281359 A1 | 11/2008 | Abdou |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2008/0287997 A1 | 11/2008 | Altarac et al. |
| 2008/0288072 A1 | 11/2008 | Kohm |
| 2008/0288075 A1 | 11/2008 | Zucherman et al. |
| 2008/0288078 A1 | 11/2008 | Kohm et al. |
| 2008/0294199 A1 | 11/2008 | Kohm et al. |
| 2008/0294200 A1 | 11/2008 | Kohm et al. |
| 2008/0294204 A1 | 11/2008 | Chirico et al. |
| 2008/0294263 A1 | 11/2008 | Altarac et al. |
| 2008/0300686 A1 | 12/2008 | Khoo |
| 2008/0300687 A1 | 12/2008 | Lin et al. |
| 2008/0312741 A1 | 12/2008 | Lee et al. |
| 2008/0319549 A1 | 12/2008 | Greenhalgh et al. |
| 2008/0319550 A1 | 12/2008 | Altarac et al. |
| 2009/0005819 A1 | 1/2009 | Ben-Mokhtar et al. |
| 2009/0005873 A1 | 1/2009 | Slivka et al. |
| 2009/0012528 A1 | 1/2009 | Aschmann et al. |
| 2009/0012614 A1 | 1/2009 | Dixon |
| 2009/0018658 A1 | 1/2009 | Garcia |
| 2009/0018662 A1 | 1/2009 | Pasquet et al. |
| 2009/0030523 A1 | 1/2009 | Taylor |
| 2009/0036925 A1 | 2/2009 | Sala et al. |
| 2009/0043342 A1 | 2/2009 | Freedland |
| 2009/0054931 A1 | 2/2009 | Metz-Stavenhagen |
| 2009/0054988 A1 | 2/2009 | Hess |
| 2009/0062915 A1 | 3/2009 | Kohm et al. |
| 2009/0062918 A1 | 3/2009 | Wang et al. |
| 2009/0082808 A1 | 3/2009 | Butler et al. |
| 2009/0093817 A1 | 4/2009 | Zucherman et al. |
| 2009/0093843 A1 | 4/2009 | Lemoine et al. |
| 2009/0093883 A1 | 4/2009 | Carrasco |
| 2009/0099603 A1 | 4/2009 | Nishida |
| 2009/0105761 A1 | 4/2009 | Robie |
| 2009/0105773 A1 | 4/2009 | Lange et al. |
| 2009/0112266 A1 | 4/2009 | Weng et al. |
| 2009/0118833 A1 | 5/2009 | Hudgins et al. |
| 2009/0138045 A1 | 5/2009 | Ciupik et al. |
| 2009/0138046 A1 | 5/2009 | Altarac et al. |
| 2009/0138087 A1 | 5/2009 | Miglietta et al. |
| 2009/0149885 A1 | 6/2009 | Durward et al. |
| 2009/0149886 A1 | 6/2009 | Zentes et al. |
| 2009/0171399 A1 | 7/2009 | White et al. |
| 2009/0198241 A1 | 8/2009 | Phan |
| 2009/0198277 A1 | 8/2009 | Gordon et al. |
| 2009/0198278 A1 | 8/2009 | Shibata et al. |
| 2009/0198337 A1 | 8/2009 | Phan |
| 2009/0198338 A1 | 8/2009 | Phan |
| 2009/0209965 A1 | 8/2009 | Lewis |
| 2009/0216274 A1 | 8/2009 | Morancy-meister et al. |
| 2009/0222043 A1 | 9/2009 | Altarac et al. |
| 2009/0234389 A1 | 9/2009 | Chuang et al. |
| 2009/0240280 A1 | 9/2009 | Wang et al. |
| 2009/0240283 A1 | 9/2009 | Carls et al. |
| 2009/0248076 A1 | 10/2009 | Reynolds et al. |
| 2009/0248079 A1 | 10/2009 | Kwak et al. |
| 2009/0248081 A1 | 10/2009 | Lehuec et al. |
| 2009/0254122 A1 | 10/2009 | Khalife |
| 2009/0254185 A1 | 10/2009 | Döllinger |
| 2009/0259316 A1 | 10/2009 | Ginn et al. |
| 2009/0265006 A1 | 10/2009 | Seifert et al. |
| 2009/0270919 A1 | 10/2009 | Dos Reis, Jr. |
| 2009/0275982 A1 | 11/2009 | Taylor |

(56) References Cited

U.S. PATENT DOCUMENTS

| | | |
|---|---|---|
| 2009/0281626 A1 | 11/2009 | Farr |
| 2009/0292314 A1 | 11/2009 | Mangione et al. |
| 2009/0292315 A1 | 11/2009 | Trieu |
| 2009/0292316 A1 | 11/2009 | Hess |
| 2009/0292317 A1 | 11/2009 | Belliard |
| 2009/0297603 A1 | 12/2009 | Joshi |
| 2009/0306715 A1 | 12/2009 | Jackson et al. |
| 2009/0306716 A1 | 12/2009 | Beger et al. |
| 2009/0318967 A1 | 12/2009 | Jeon et al. |
| 2009/0326581 A1 | 12/2009 | Galley et al. |
| 2010/0004688 A1 | 1/2010 | Maas et al. |
| 2010/0004744 A1 | 1/2010 | Zucherman et al. |
| 2010/0010546 A1 | 1/2010 | Hermida Ochoa |
| 2010/0010548 A1 | 1/2010 | Hermida Ochoa |
| 2010/0036419 A1 | 2/2010 | Patel et al. |
| 2010/0174373 A1 | 7/2010 | Galley et al. |
| 2010/0191287 A1 | 7/2010 | Bucci |
| 2010/0211101 A1 | 8/2010 | Blackwell et al. |
| 2010/0222817 A1 | 9/2010 | Perez-Cruet et al. |
| 2010/0241167 A1 | 9/2010 | Taber et al. |
| 2011/0029020 A1 | 2/2011 | Gordon et al. |
| 2011/0054531 A1 | 3/2011 | Lamborne et al. |
| 2011/0066186 A1 | 3/2011 | Boyer, II et al. |
| 2011/0144692 A1* | 6/2011 | Saladin .............. A61B 17/7053 606/249 |
| 2011/0166600 A1 | 7/2011 | Lamborne et al. |
| 2011/0172711 A1 | 7/2011 | Kirschman |
| 2011/0264221 A1 | 10/2011 | Woodward et al. |
| 2011/0313458 A1 | 12/2011 | Butler et al. |
| 2011/0319936 A1 | 12/2011 | Gordon et al. |
| 2012/0016418 A1 | 1/2012 | Chin et al. |
| 2013/0012996 A1* | 1/2013 | Zamani .............. A61B 17/7068 606/248 |
| 2015/0351813 A1 | 12/2015 | Lamborne et al. |
| 2016/0120579 A1 | 5/2016 | Lamborne et al. |
| 2016/0354123 A1 | 12/2016 | Lamborne et al. |

FOREIGN PATENT DOCUMENTS

| | | | |
|---|---|---|---|
| JP | H0737112 U | * | 7/1995 |
| JP | 2003220071 A | | 8/2003 |
| JP | 2003523214 A | | 8/2003 |
| JP | 2005525907 A | | 9/2005 |
| JP | 2008539819 A | | 11/2008 |
| KR | 20060124851 A | | 12/2006 |
| WO | WO-9400062 A1 | | 1/1994 |
| WO | WO 03099147 A1 | | 12/2003 |
| WO | WO-03099147 A1 | | 12/2003 |
| WO | WO-2004039239 A2 | | 5/2004 |
| WO | WO-2005009300 A1 | | 2/2005 |
| WO | WO-2005055868 A2 | | 6/2005 |
| WO | WO-2006102269 A2 | | 9/2006 |
| WO | WO-2006119235 A1 | | 11/2006 |
| WO | WO-2007019391 A2 | | 2/2007 |
| WO | WO-2008067452 A1 | | 6/2008 |
| WO | WO-2008086533 A2 | | 7/2008 |
| WO | WO-2008088613 A2 | | 7/2008 |
| WO | WO-2008124831 A2 | | 10/2008 |
| WO | WO-2009058439 A1 | | 5/2009 |
| WO | WO-2011019756 A2 | | 2/2011 |
| WO | WO-2011019756 A3 | | 2/2011 |
| WO | WO-2011019758 A2 | | 2/2011 |
| WO | WO-2011019758 A3 | | 2/2011 |

OTHER PUBLICATIONS

"U.S. Appl. No. 11/934,604, Examiner Interview Summary mailed Feb. 27, 2012", 3 pgs.

"U.S. Appl. No. 11/934,604, Examiner Interview Summary mailed Sep. 1, 2011", 3 pgs.

"U.S. Appl. No. 11/934,604, Final Office Action mailed Apr. 24, 2012", 42 pgs.

"U.S. Appl. No. 11/934,604, Non Final Office Action mailed Apr. 13, 2011", 34 pgs.

"U.S. Appl. No. 11/934,604, Non Final Office Action mailed Oct. 19, 2011", 43 pgs.

"U.S. Appl. No. 11/934,604, Notice of Allowance mailed Jun. 19, 2012", 10 pgs.

"U.S. Appl. No. 11/934,604, Notice of Non-Compliant Amendment mailed Feb. 3, 2012", 2 pgs.

"U.S. Appl. No. 11/934,604, Preliminary Amendment filed Mar. 4, 2011", 11 pgs.

"U.S. Appl. No. 11/934,604, Response filed Feb. 21, 2012 to Non Final Office Action mailed Oct. 19, 2011", 37 pgs.

"U.S. Appl. No. 11/934,604, Response filed Mar. 22, 2011 to Restriction Requirement mailed Feb. 24, 2011", 1 pgs.

"U.S. Appl. No. 11/934,604, Response filed May 21, 2012 to Final Office Action mailed Apr. 24, 2012", 13 pgs.

"U.S. Appl. No. 11/934,604, Response filed Jul. 13, 2011 to Non Final Office Action mailed Apr. 13, 2011", 28 pgs.

"U.S. Appl. No. 11/934,604, Restriction Requirement mailed Feb. 24, 2011", 12 pgs.

"U.S. Appl. No. 13/460,738, Appeal Brief filed Oct. 7, 2013", 22 pgs.

"U.S. Appl. No. 13/460,738, Reply Brief filed Mar. 21, 2014", 4 pgs.

"U.S. Appl. No. 13/460,738, Response filed Dec. 27, 2012 to Non Final Office Action mailed Jul. 27, 2012", 15 pgs.

"U.S. Appl. No. 14/739,170, Non Final Office Action mailed Jul. 14, 2016", 13 pgs.

"U.S. Appl. No. 14/739,170, Response filed Jun. 30, 2016 to Restriction Requirement mailed Apr. 5, 2016", 7 pgs.

"U.S. Appl. No. 14/992,320, Response filed Aug. 3, 2016 to Non Final Office Action mailed Apr. 7, 2016", 9 pgs.

"Australian Application Serial No. 2007343630, First Examiner Report mailed Jun. 28, 2012", 5 pgs.

"Australian Application Serial No. 2007343630, Notice of Acceptance mailed Dec. 2, 2013", 1 pgs.

"Chinese Application Serial No. 200780052120.4, Office Action mailed Mar. 24, 2011", (W/ English Translation), 10 pgs.

"Chinese Application Serial No. 200780052120.4, Office Action mailed Apr. 27, 2012", (W/ English Translation), 6 pgs.

"Chinese Application Serial No. 200780052120.4, Response filed Jul. 11, 2012 to Office Action mailed Apr. 27, 2012", (W/ English Translation), 12 pgs.

"Chinese Application Serial No. 200780052120.4, Response filed Nov. 8, 2011 to Office Action mailed Mar. 24, 2011", (W/ English Translation), 15 pgs.

"Definition for "around"", [Online] retrieved from the internet:www.thefreedictionary.com [accessed on Oct. 6, 2011], [Online] retrieved from the internet:www.thefreedictionary.com, (Oct. 6, 2011), 2 pgs.

"Definition for deform", [Online] retrieved from the Internet: <http://dictionary.reference.com>, (Apr. 26, 2012), 2 pgs.

"European Application Serial No. 07854667.8, Communication Pursuant to Article 94(3) EPC mailed Jul. 2, 2015", 4 pgs.

"European Application Serial No. 07854667.8, Extended European Search Report mailed Mar. 12, 2012", 10 pgs.

"European Application Serial No. 07854667.8, Response filed Jan. 17, 2016 to Communication Pursuant to Article 94(3) EPC mailed Oct. 9, 2015", 11 pgs.

"European Application Serial No. 07854667.8, Response filed Oct. 8, 2012 to Extended European Search Report mailed Mar. 12, 2012", 14 pgs.

"European Application Serial No. 13180855.2, Decision to grant mailed Dec. 17, 2015", 2 pgs.

"European Application Serial No. 13180855.2, Office Action mailed Jul. 23, 2015", 43 pgs.

"European Application Serial No. 13180855.2, Response filed May 27, 2014 to Extended European Search Report mailed Oct. 7, 2013", 10 pgs.

"International Application Serial No. PCT/US2007/084856, International Preliminary Report on Patentability mailed Jul. 14, 2009", 9 pgs.

(56) References Cited

OTHER PUBLICATIONS

"International Application Serial No. PCT/US2008/070353, International Search Report and Written Opinion mailed Nov. 10, 2008", (Nov. 10, 2008), 16 pgs.
"Japanese Application Serial No. 2009-545544, Amendment filed Nov. 12, 2010", W/ English Translation, 19 pgs.
"Japanese Application Serial No. 2009-545544, Office Action mailed Mar. 5, 2013", (W/ English Translation), 4 pgs.
"Japanese Application Serial No. 2009-545544, Office Action mailed Jun. 19, 2012", (W/ English Translation), 8 pgs.
"Japanese Application Serial No. 2009-545544, Response filed Nov. 7, 2012 to Office Action mailed Jun. 19, 2012", W/ English Translation, 15 pgs.
"The First Minimally Invasive Solution to Lumbar Spine Stenosis", Kyphon X-Stop IPD System, (2007), 4 pgs.
"X-Stop a Patient's Guide Lumbar Spinal Stenosis & X-Stop Interspinous Decompression", Kyphon, (2002), 16 pgs.
Bostman, et al., "Posterior Spinal Fusion Using Internal Fixation with the Daab Plate", (1984), 310-314.
Bostman, O, et al., "Acta Orthop Scand article", (Jun. 1984), 6 pgs.
Knowles, F. L, "The Knowles Vertebral Support Orientation", Journal of Iowa State Medical Society, XLVIII(10), (Oct. 1958), 551-554.
Lee, et al., "An Interspinous Process Distractor (X Stop) for Lumbar Spinal Stenosis in Elderly Patients", J. Spinal Discord Tech., vol. 17, No. 1, (Feb. 2004), 72-77.
Wang, et al., "Comparison of CD Horizon Spire Spinous Process Plate Stabilization and Pedicle Screw Fixation After Anterior Lumbar Interbody Fusion", Journal of Neurosurg Spine, vol. 4, (Feb. 4, 2006), 132-136.
Wang, Jermey C, et al., "Spire Spinous Process Stabilization Plate: Bio-Chemical Evaluation of a Novel Technology", Journal of Neurosurg Spine, vol. 4, (Feb. 4, 2006), 160-164.
"U.S. Appl. No. 12/020,282, Applicant's Summary of Examiner Interview filed Feb. 28, 2012", 1 pg.
"U.S. Appl. No. 12/020,282, Examiner Interview Summary mailed Feb. 23, 2012", 3 pgs.
"U.S. Appl. No. 12/020,282, Final Office Action mailed May 11, 2012", 35 pgs.
"U.S. Appl. No. 12/020,282, Final Office Action mailed Dec. 5, 2014", 18 pgs.
"U.S. Appl. No. 12/020,282, Non Final Office Action mailed Apr. 17, 2014", 34 pgs.
"U.S. Appl. No. 12/020,282, Non Final Office Action mailed Nov. 23, 2011", 11 pgs.
"U.S. Appl. No. 12/020,282, Notice of Non-Compliant Amendment mailed Oct. 16, 2012", 2 pgs.
"U.S. Appl. No. 12/020,282, Response filed Jan. 26, 2015 to Final Office Action mailed Dec. 5, 2014", 13 pgs.
"U.S. Appl. No. 12/020,282, Response filed Feb. 23, 2012 to Non Final Office Action mailed Nov. 23, 2011", 16 pgs.
"U.S. Appl. No. 12/020,282, Response filed Sep. 12, 2014 to Non Final Office Action mailed Apr. 17, 2014", 25 pgs.
"U.S. Appl. No. 12/020,282, Response filed Oct. 11, 2012 to Final Office Action mailed May 11, 1", 22 pgs.
"U.S. Appl. No. 12/020,282, Response filed Oct. 30, 2012 to Notice of Non-Compliant Amendment mailed Oct. 16, 2012", 22 pgs.
"U.S. Appl. No. 12/020,282, Response filed Nov. 14, 2011 to Restriction Requirement mailed Jul. 14, 2011", 1 pg.
"U.S. Appl. No. 12/020,282, Restriction Requirement mailed Jul. 14, 2011", 7 pgs.
"U.S. Appl. No. 13/460,738, Appeal Decision mailed Jun. 24, 2016", 12 pgs.
"U.S. Appl. No. 14/739,170, Preliminary Amendment filed Jun. 15, 2015", 10 pgs.
"U.S. Appl. No. 14/739,170, Restriction Requirement mailed Apr. 5, 2016", 6 pgs.
"U.S. Appl. No. 14/992,323, Non Final Office Action mailed Apr. 7, 2016", 15 pgs.
"U.S. Appl. No. 14/992,323, Preliminary Amendment filed Jan. 12, 2016", 6 pgs.
"Australian Application serial No. 2008319176, First Examiner Report mailed Mar. 19, 2013", 4 pgs.
"Australian Application Serial No. 2008319176, Voluntary Amendment filed May 31, 2010", 24 pgs.
"Chinese Application Serial No. 2008801238560, Office Action mailed Jul. 27, 2012", (W/ English Translation), 17 pgs.
"Chinese Application Serial No. 2008801238560, Response filed Feb. 16, 2013 to Office Action mailed Jul. 27, 2012", (W/ English Translation), 18 pgs.
"European Application Serial No. 08727627.5, Extended European Search Report mailed Mar. 12, 2012", 6 pgs.
"International Application Serial No. PCT/US2007/084856, International Search Report mailed Oct. 10, 2008", 2 pgs.
"International Application Serial No. PCT/US2007/084856, Written Opinion mailed Oct. 10, 2008", 8 pgs.
"International Application Serial No. PCT/US2008/070353, International Search Report mailed Nov. 10, 2008", 2 pgs.
"International Application Serial No. PCT/US2008/070353, Written Opinion mailed Nov. 10, 2008", 9 pgs.
U.S. Appl. No. 12/013,351, filed Jan. 11, 2008, Spinous Implants and Methods.
U.S. Appl. No. 13/460,738, filed Apr. 30, 2012, Spinous Process Implants and Associated Methods.
U.S. Appl. No. 12/751,856, filed Mar. 31, 2010, Spinous Process Implants and Associated Methods.
U.S. Appl. No. 12/854,125, filed Aug. 10, 2010, Interspinsous Implants and Methods.
U.S. Appl. No. 14/739,170, filed Jun. 15, 2015, Spinal Implants and Methods.
"U.S. Appl. No. 12/020,282, Notice of Allowance mailed Feb. 12, 2015", 9 pgs.
"U.S. Appl. No. 12/751,856, Examiner Interview Summary mailed Feb. 23, 2012", 3 pgs.
"U.S. Appl. No. 12/751,856, Examiner Interview Summary mailed Jun. 1, 2015", 3 pgs.
"U.S. Appl. No. 12/751,856, Examiner Interview Summary mailed Dec. 11, 2015", 3 pgs.
"U.S. Appl. No. 12/751,856, Final Office Action mailed May 11, 2012", 46 pgs.
"U.S. Appl. No. 12/751,856, Final Office Action mailed Jun. 17, 2015", 28 pgs.
"U.S. Appl. No. 12/751,856, Non Final Office Action mailed Apr. 22, 2014", 45 pgs.
"U.S. Appl. No. 12/751,856, Non Final Office Action mailed Oct. 28, 2011", 10 pgs.
"U.S. Appl. No. 12/751,856, Non-Final Office Action mailed Dec. 29, 2014", 36 pgs.
"U.S. Appl. No. 12/751,856, Notice of Allowance mailed Sep. 28, 2015", 5 pgs.
"U.S. Appl. No. 12/751,856, Response filed Feb. 28, 2012 to Non Final Office Action mailed Oct. 28, 2011", 4 pgs.
"U.S. Appl. No. 12/751,856, Response filed May 28, 2015 to Non Final Office Action mailed Dec. 29, 2014", 15 pgs.
"U.S. Appl. No. 12/751,856, Response filed Aug. 13, 2012 to Final Office Action mailed May 11, 2012", 25 pgs.
"U.S. Appl. No. 12/751,856, Response filed Sep. 17, 2015 to Final Office Action mailed Jun. 17, 2015", 11 pgs.
"U.S. Appl. No. 12/751,856, Response filed Sep. 22, 2014 to Non Final Office Action mailed Apr. 22, 2014", 17 pgs.
"U.S. Appl. No. 12/854,125, Applicant's Summary of Examiner Interview filed Mar. 21, 2012", 1 pg.
"U.S. Appl. No. 12/854,125, Examiner Interview Summary mailed Feb. 23, 2012", 3 pgs.
"U.S. Appl. No. 12/854,125, Examiner Interview Summary mailed Jun. 2, 2015", 3 pgs.
"U.S. Appl. No. 12/854,125, Final Office Action mailed Apr. 24, 2012", 43 pgs.
"U.S. Appl. No. 12/854,125, Final Office Action mailed Dec. 31, 2014", 52 pgs.
"U.S. Appl. No. 12/854,125, Non Final Office Action mailed Jun. 26, 2014", 41 pgs.

(56) References Cited

OTHER PUBLICATIONS

"U.S. Appl. No. 12/854,125, Non Final Office Action mailed Oct. 31, 2011", 9 pgs.
"U.S. Appl. No. 12/854,125, Notice of Allowance mailed Oct. 7, 2015", 9 pgs.
"U.S. Appl. No. 12/854,125, Response filed Feb. 21, 2012 to Non Final Office Action mailed Oct. 31, 2011", 9 pgs.
"U.S. Appl. No. 12/854,125, Response filed Jun. 1, 2015 to Final Office Action mailed Dec. 31, 2014", 30 pgs.
"U.S. Appl. No. 12/854,125, Response filed Aug. 24, 2012 to Final Office Action mailed Apr. 24, 2012", 38 pgs.
"U.S. Appl. No. 12/854,125, Response filed Sep. 25, 2014 to Non Final Office Action mailed Jun. 26, 2014", 20 pgs.
"U.S. Appl. No. 13/460,738, Examiner's Answer mailed Jan. 21, 2014", 28 pgs.
"U.S. Appl. No. 13/460,738, Final Office Action mailed Apr. 3, 2013", 33 pgs.
"U.S. Appl. No. 13/460,738, Non Final Office Action mailed Jul. 27, 2012", 34 pgs.
"Chinese Application Serial No. 2010800455863, Office Action mailed Jun. 26, 2015", (W/ English Translation), 17 pgs.
"Defendant Pioneer Surgical Technology", Civil Action No. 1:13-cv-01035-WJM-BNB, (Jul. 31, 2013), 27 pgs.
"European Application Serial No. 10759359.2, Extended European Search Report mailed Nov. 26, 2013", 6 pgs.
"European Application Serial No. 10759359.2, Office Action mailed Nov. 26, 2013", 1 pg.
"European Application Serial No. 13180855.2, Extended European Search Report mailed Oct. 7, 2013", 4 pgs.
"International Application Serial No. PCT/US2008/050931, International Preliminary Report on Patentability mailed Apr. 5, 2010", 5 pgs.
"International Application Serial No. PCT/US2008/070353, International Preliminary Report on Patentability mailed Apr. 5, 2010", 10 pgs.
"International Application Serial No. PCT/US2008/070353, Notification Concerning Transmittal of International Preliminary Report on Patentability (Chapter I of the Patent Cooperation Treaty) mailed May 14, 2010", 11 pgs.
U.S. Appl. No. 13/584,661, filed Aug. 13, 2012, Spinous Process Implants and Associated Methods.
U.S. Appl. No. 13/774,243, filed Feb. 22, 2013, Spinous Process Implants, Instruments, and Methods.
U.S. Appl. No. 14/992,323, filed Jan. 11, 2016, Interspinsous Implants and Methods.
U.S. Appl. No. 15/242,960, filed Aug. 22, 2016, Spinous Process Implants and Associated Methods.
"U.S. Appl. No. 12/538,710, Non Final Office Action mailed Feb. 6, 2012", 72 pgs.
"U.S. Appl. No. 12/538,710, Notice of Allowance mailed Nov. 16, 2012", 16 pgs.
"U.S. Appl. No. 12/538,710, Preliminary Amendment filed Aug. 21, 2009", 6 pgs.
"U.S. Appl. No. 12/538,710, Response filed Jan. 9, 2012 to Restriction Requirement mailed Nov. 9, 2011", 3 pgs.
"U.S. Appl. No. 12/538,710, Response filed Jul. 6, 2012 to Non Final Office Action mailed Feb. 6, 2012", 59 pgs.
"U.S. Appl. No. 12/538,710, Restriction Requirement mailed Nov. 9, 2011", 15 pgs.
"U.S. Appl. No. 14/739,170, Notice of Allowance mailed Nov. 23, 2016", 13 pgs.
"U.S. Appl. No. 14/739,170, Response filed Oct. 13, 2016 to Non-Final Office Action mailed Jul. 14, 2016", 12 pgs.
"U.S. Appl. No. 14/992,323, Notice of Allowance mailed Sep. 7, 2016", 9 pgs.
"U.S. Appl. No. 14/992,323, Notice of Allowance mailed Dec. 22, 2016", 9 pgs.
"Australian Application Serial No. 2008204769, Non Final Office Action mailed Jun. 28, 2012", 3 pgs.
"Chinese Application Serial No. 2010800455863, Response filed Nov. 3, 2015 to Office Action mailed Jun. 26, 2015", W/ English Claims, 10 pgs.
"European Application Serial No. 08727627.5, Resposne filed Oct. 8, 2012 to Extended European Search Report mailed Mar. 12, 2012", 12 pgs.
"European Application Serial No. 10808656.2, Extended European Search Report mailed Jul. 7, 2014", 7 pgs.
"European Application Serial No. 10808656.2, Response filed Jan. 23, 2015 to Extended European Search Report mailed May 12, 2011", 11 pgs.
"Indian Application Serial No. 4465/DELNP/2009, First Examiner Report mailed Sep. 15, 2016", 12 pgs.
"International Application No. PCT/US2010/045079, International Preliminary Report on Patentability mailed Feb. 14, 2012", 4 pgs.
"International Application No. PCT/US2010/045079, International Search Report mailed Apr. 22, 2011", 10 pgs.
"International Application No. PCT/US2010/045079, Written Opinion mailed Apr. 22, 2011", 3 pgs.
"International Application No. PCT/US2010/045081, International Preliminary Report on Patentability mailed Feb. 14, 2012", 4 pgs.
"International Application No. PCT/US2010/045081, International Search Report Apr. 22, 2011", 10 pgs.
"International Application No. PCT/US2010/045081, Written Opinion Apr. 22, 2011", 3 pgs.
"International Application Serial No. PCT/US2008/050931, International Preliminary Report on Patentability mailed Mar. 19, 2010", 3 pgs.
"International Application Serial No. PCT/US2008/050931, International Search Report mailed Jul. 28, 2008", pgs.
"International Application Serial No. PCT/US2008/050931, Written Opinion mailed Jul. 28, 2008", 3 pgs.
"Japanese Application Serial No. 2009-545544, Response filed Jun. 18, 2013 to Office Action mailed Mar. 5, 2013", W/ Machine Translation, 12 pgs.
U.S. Appl. No. 15/407,547, filed Jan. 17, 2017, Interspinsous Implants and Methods.

* cited by examiner

SPINOUS PROCESS IMPLANTS AND ASSOCIATED METHODS

CROSS-REFERENCE TO RELATED APPLICATIONS

This application is a continuation of U.S. patent application Ser. No. 12/751,856, filed Mar. 31, 2010, which is now issued as U.S. Pat. No. 9,247,968, which is a continuation-in-part of U.S. patent application Ser. No. 11/934,604, filed Nov. 2, 2007, which is now issued as U.S. Pat. No. 8,241,330, which claims the benefit of U.S. Provisional Application No. 60/912,273, filed Apr. 17, 2007 and U.S. Provisional Application No. 60/884,581, filed Jan. 11, 2007, all of which are hereby incorporated by reference in their entirety. This application further claims the benefit of U.S. Provisional Application No. 61/165,354, filed Mar. 31, 2009, which is hereby incorporated by reference in its entirety.

FIELD OF THE INVENTION

The present invention relates to spinous process implants and associated methods.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age, spinal discs begin to break down, or degenerate resulting in the loss of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions are collectively referred to herein as spine disease.

Conventionally, surgeons treat spine disease by attempting to restore the normal spacing between adjacent vertebrae. This may be sufficient to relieve pressure from affected nerve tissue. However, it is often necessary to also surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

More recently, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed.

SUMMARY

The present invention provides a spinous process implant and associated methods.

In one aspect of the invention, an implant for placement between spinous processes of adjacent vertebrae includes a spacer and an extension. The spacer has a sidewall with superior and inferior surfaces operable to abut the spinous processes and maintain the spinous processes in spaced apart relationship. In one example, the sidewall extends generally parallel to a longitudinal axis. In other examples, the sidewall may converge, diverge, or define any other suitable shape relative to a longitudinal axis. The sidewall may be cylindrical, tapered, symmetrical, and/or asymmetrical relative to a longitudinal axis. The extension projects from the spacer transverse to the longitudinal axis to lie generally alongside the spinous processes of adjacent vertebrae and engage the spinous processes to limit the maximum spacing between the spinous processes.

In another aspect of the invention, the extension includes an adjustable fastener.

In another aspect of the invention, the extension includes a removable fastener.

In another aspect of the invention, an implant for placement between spinous processes of adjacent vertebrae includes a spacer having at least one transverse opening communicating from at least one of a superior and inferior outer surface inwardly to facilitate tissue in-growth.

In another aspect of the invention, the spacer includes a hollow interior and a plurality of transverse openings communicating from the superior and inferior outer surfaces to the hollow interior to facilitate tissue growth.

In another aspect of the invention, the spacer includes a porous structure and the transverse openings comprise a plurality of pores.

In another aspect of the invention, an implant for placement between spinous processes of adjacent vertebrae of a spine includes a spacer and separate extensions engageable with the spacer at its ends. The spacer is provided in a variety of lengths and superior to inferior surface spacings.

In another aspect of the invention, an implant for placement between spinous processes of adjacent vertebrae of a spine includes a spacer and a cerclage element. The cerclage element is offset posteriorly of the midline in use so that the spacer defines a fulcrum and the cerclage element is extendible around a portion of a vertebra and operative to impart a moment to the vertebra about the spacer.

In another aspect of the invention, instrumentation includes two instruments each having a working portion tapering from a larger cross-sectional dimension nearer a handle to a smaller cross-sectional dimension near the free end. The free end of one of the instruments defines a hollow tip sized to engage the free end of the first instrument and sized to engage the hollow tip of the implant.

In another aspect of the invention, a method includes inserting a spacer between spinous processes of adjacent vertebrae to provide both an extension stop and a flexion stop.

In another aspect of the invention, a method includes inserting a spacer between spinous processes of adjacent vertebrae and connecting a cerclage element to the adjacent vertebrae to impart a moment to the vertebrae about the spacer.

In another aspect of the invention, a method includes inserting a tapered instrument between adjacent spinous processes: engaging a tip of a spinous process spacer with the tip of the tapered instrument and passing the engaged pair back between the adjacent spinous process to insert the spacer between the spinous processes.

In another aspect of the invention, extensions may be provided that are shaped to allow extensions on adjacent implants to interleave.

In another aspect of the invention, extensions may be provided that permit an extension of one implant to overlie an extension of an adjacent implant.

In another aspect of the invention, an implant for placement between spinous processes may be shaped to accommodate a small or missing spinous process such as, e.g., on the sacrum of a patient.

In another aspect of the invention, an implant for placement between spinous processes may include a spacer that has a variable height.

In another aspect of the invention, an implant for placement between spinous processes may include a mechanism operable to distract adjacent spinous processes away from one another.

In another aspect of the invention, an implant for placement between spinous processes may include bone gripping extensions and a mechanism operable to simultaneously lock a desired horizontal spacing between extensions on opposing sides of a single spinous process and a desired vertical spacing between extensions engaged with adjacent spinous processes.

In another aspect of the invention, an implant for placement between spinous processes may include a spacers and/or extensions engageable with more man two spinous processes to constrain the motion of multiple spinal levels.

In another aspect of the invention, an implant for placement between spinous processes may include first and second spacers. The first and second spacers may be made of different materials.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
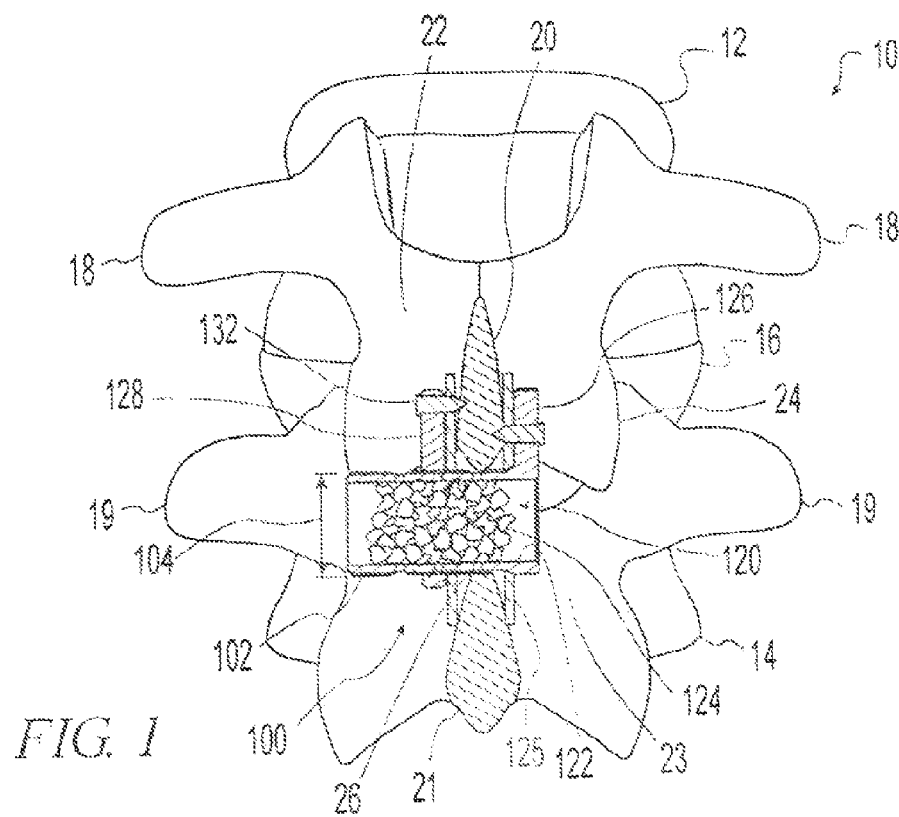
FIG. 1 is across sectional view of an implant according to the present invention in situ.

Embodiments of spinous process implants according to the present invention include a spacer and an extension extending outwardly from the spacer. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances.

The spacer may have any suitable cross-sectional shape. For example, it may be cylindrical, D-shaped, C-shaped, H-shaped, include separated cantilevered beams, and/or any other suitable shape. The shape may include chamfers, fillets, flats, relief cuts, and/or other features to accommodate anatomical features such as for example the laminae and/or facets. The spacer may have a sidewall that is generally parallel, tapered, or irregularly shaped. The spacer may have a fixed height or it may have a variable height allowing for adjustment intraoperatively. A single spacer may be provided for a single level of spine correction or multiple spacers may be provided for a single level or multiple levels of spine correction. Where multiple spacers are provided, they may be made of the same or different materials.

The extension may extend transversely from the spacer relative to a spacer longitudinal axis to maintain the spacer between adjacent spinous processes. A single extension may extend in one or more directions or multiple extensions may be provided that extend in multiple directions. One or more extensions may be adjustable longitudinally relative to one another and/or the spacer to allow the extensions to be positioned relative to the spinous processes. A moveable extension may be provided that is movable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation.

Extensions may be provided that permit an extension of one implant to overlie, or overlap, an extension of an adjacent implant. For example, the extensions may overlap similar to shingles overlapping. The extensions may be offset to further facilitate the overlapping of adjacent extensions. The extensions may have smooth surfaces that facilitate relative motion between overlapping portions of extensions. The extensions may have surfaces that engage one another to resist relative motion; for example, opposing surfaces of overlapping extensions may include pads, hooks, pins, teeth, bristles, surface roughness, adhesive, holes, loops, screws, bolts, and/or other features that permit one extension to grip another.

The implant may be shaped to accommodate a small or missing spinous process such as, for example, on the sacrum of a patient. For example, a portion of one or more extensions may flare outwardly to seat on a relatively broader and/or flatter portion of a bone such as the sacrum. Such an extension may include fasteners that are longer, sharper, and/or otherwise adapted to penetrate and grip the bone. The extensions may be angularly variable relative to one another to accommodate the shape of the underlying bone.

The spacer may have a fixed height or a variable height. A variable height spacer may include a first portion and a second portion having a variable height spacing that may be locked at a desired relative spacing. The height spacing may be adjustable and/or lockable simultaneously with or independently from a horizontal bone gripping spacing of the extensions. The height spacing may be adjustable by exerting a spacing force on a first and second portion with a removable instrument and then locking the desired spacing. The height spacing may be adjustable by operation of a mechanism incorporated into the implant itself. The height spacing may be adjustable and the desired spacing locked by a single mechanism. Height spacing adjustment of the spacer may be used to distract adjacent spinous processes away from one another.

The implant may include a mechanism for compressing and/or distracting extensions toward or away from one another while they are engaged with the bone of adjacent spinous processes such that the adjacent spinous processes are similarly compressed or distracted away from one another.

The implant may include spacers and/or extensions engageable with more than two spinous processes to treat multiple spinal levels.

The spacer, extensions, and/or fasteners may advantageously be made of different materials. For example, the spacer and extensions may be made of a relatively softer material while the fasteners may be made of a relative harder material. For example, the spacer and/or extension may be made of a polymer and/or other relatively soft material and the fastener may be made of a metal and/or other relatively hard material. The different materials may have different transmission properties such that one may appear well defined on a medical image and the other appear only dimly or not at all. For example, a metal portion of an implant will show plainly on an x-ray whereas a polymer portion will be much fainter. These properties can be used to allow a surgeon to see that certain portions, e.g. fasteners, are engaged with bone while allowing a clear view through other portions to visualize the treatment site, e.g., the space between bones.

Cerclage may be used to stabilize the spinous process implant and/or to provide other benefits. For example, wires, straps, bands, cables, cords, and/or other elongated members may encircle the pedicles, laminae, spinous processes, transverse processes, and/or other spinal structures. The cerclage may be relatively inextensible to provide a hard check to spine flexion or the cerclage may be relatively extensible to provide increasing resistance to flexion. The cerclage may be relatively flexible and drapeable such as a woven fabric or it may be relatively rigid such as a metal band. The cerclage may have shape memory properties that cause it to resume a prior set shape after implantation. The cerclage may be independent of the spinous process implant or may engage it. For example, the cerclage may pass through a hollow interior of the spinous process implant and/or engage the extension. The cerclage may be offset from the spacer and provide a tensioning force that uses the spacer as a fulcrum to offload the disc and/or open the disc space.

The implant may be supplemented with bone growth promoting substances to facilitate fusion of adjacent vertebrae between spinous processes, laminae, transverse processes, facets, and/or other spinal structures. The bone growth promoting substances may be spaced from the implant, placed adjacent the implant, sandwiched between the implant and underlying bone, placed inside the implant, coated onto the implant and/or otherwise placed relative to the implant. If it is coated onto the implant it may cover the entire implant or only selected portions of the implant such as the extensions, fasteners, spinous process contacting portions of the spacer, and/or other portions.

In addition, bone growth promoting substances may include structural members that contribute directly to the support of the spacing between adjacent vertebrae. For example, a structural bone graft may be incorporated into, onto, around, and/or otherwise associated with the spacer and/or extensions to both provide structural support and a scaffold for new bone formation. For example, a structural piece of bone may engage with the spacer and extend beyond the spacer such that adjacent spinous processes rest on the structural bone.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, other ceramics, and/or other suitable bone growth promoting substances.

The implant and any associated cerclage or other components may be made of any suitable biocompatible material including among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluropolymers, and/or other suitable biocompatible materials and combinations thereof.

The spinous process implant may be used to treat spine disease in a variety of surgical techniques including superspinous ligament sacrificing posterior approaches, superspinous ligament preserving posterior approaches, lateral approaches, and/or other suitable approaches. The spinous process implant may be used to treat spine disease by fusing adjacent vertebrae or by preserving motion between adjacent vertebrae. It may include only an extension stop such as a spacer, only a flexion stop such as flexible cerclage elements, or both a flexion and extension stop. The spinous process implant may be used to reduce loads on the facet joints, increase spinous process spacing, reduce loads on the disc, increase anterior disc spacing, and/or otherwise treat spine disease. Anterior effects may be accomplished by tensioning spine elements posterior to the spacer to apply a mechanical advantage to the spinal construct. Techniques for the spinal process implant may include leaving the tissues at the surgical site unmodified or modifying tissues such as trimming, rasping, roughening, and/or otherwise modifying tissues at the implant site.

Figure 2:
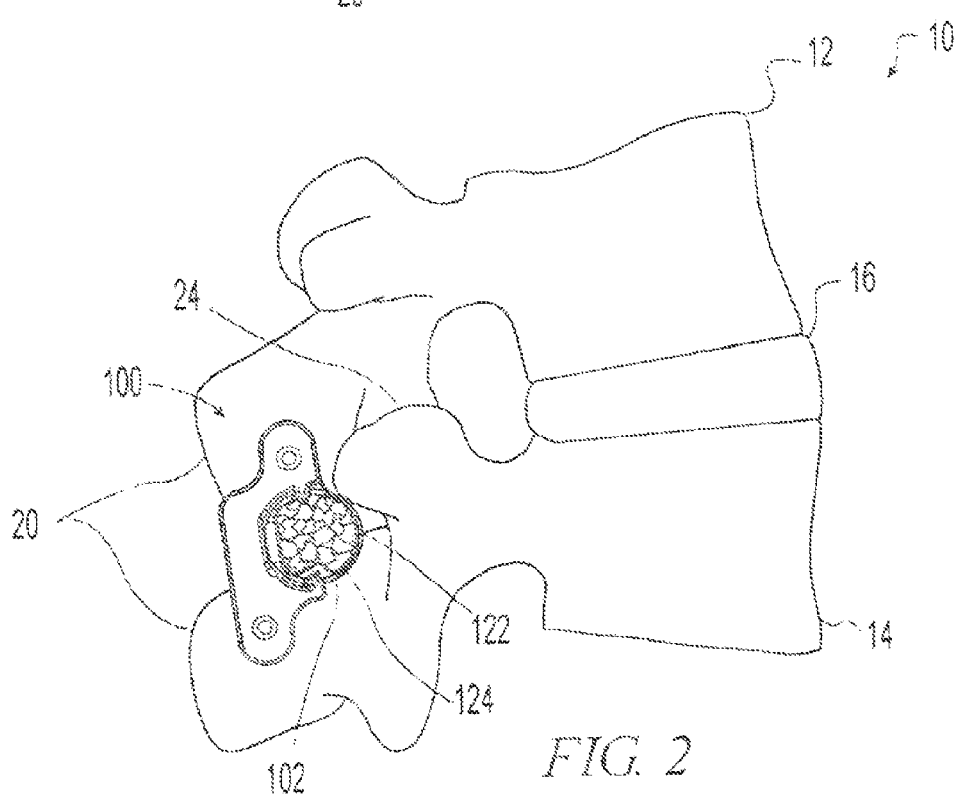
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of laminae 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The height 104 of spacer 102 limits how closely the spinous processes 20, 21 can move together. Thus, the spacer 102 maintains a minimum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
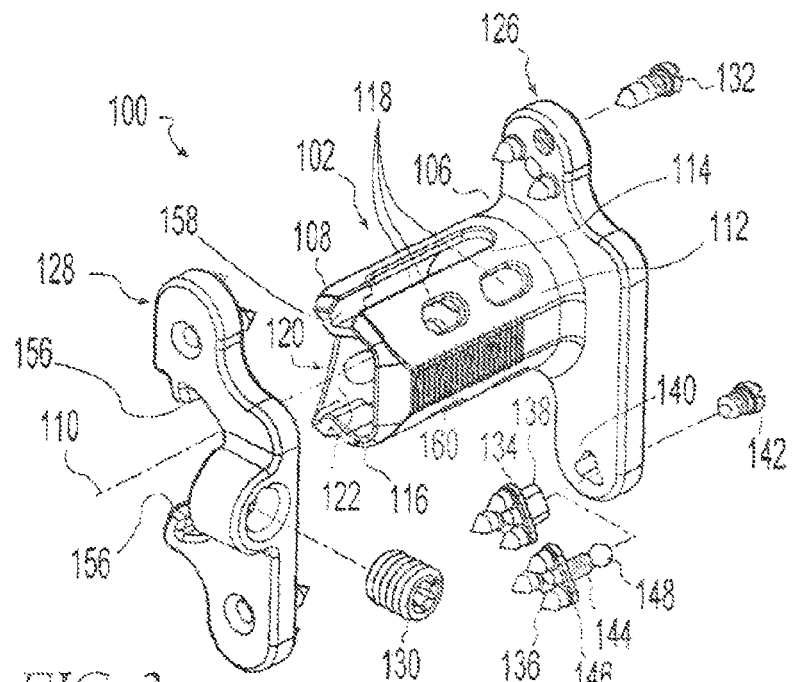
FIG. 3 is a an exploded perspective view of the implant of FIG. 1.

As shown in FIG. 3, the spacer 102 includes a first end 106, a second end 108, and a longitudinal axis 110 extending from the first end to the second end. In the illustrated example, the spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue ingrowth. The exemplary spacer 102 includes a hollow interior 120 bounded by an inner surface 122 such that the openings 118 communicate from the outer surface to the hollow interior 120. Bone growth promoting substances 124 are shown packed into the hollow interior 120 in FIGS. 1 and 2 to promote fusion of the vertebrae 12, 14 by bone growth between the spinous processes 20.

The spinous process implant 100 further includes a first extension 126 projecting outwardly from the spacer 102 transverse to the longitudinal axis 110 to lie generally alongside the superior spinous process. Abutment of the first extension 126 with the spinous process 20 helps to maintain the spacer 102 between the spinous processes 20. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous process 20 and better stabilize the implant 100. It is fixed in place by tightening a set screw 130 against the spacer 102. The extensions 126, 128 include fasteners 132, 134, 136 projecting from the extensions 126, 128 to engage the spinous process 20 to fix the spacer 102 to the spinous process 20. FIG. 1 depicts additional bone growth promoting substance in the form of a strips of bone 125 sandwiched between the extensions 126, 128 along the sides of the spinous processes 20 to promote bone growth along the sides of the spinous processes to further inhance fusion of the vertebrae 12, 14. The extensions 126, 128 preferably extend inferiorly (as shown) as well as superiorly to optionally attach to the inferior spinous processes to immobilize the spinous processes 20 relative to one another while fusion takes place.

The fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to Fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

Fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone the fastener 136 adjusts to the angle of the bone surface. The fastener 136 may also be secured such as by screw 142 to adjust the tension in the joint and/or to lock the fastener 136 in a predetermined orientation.

Figure 4:
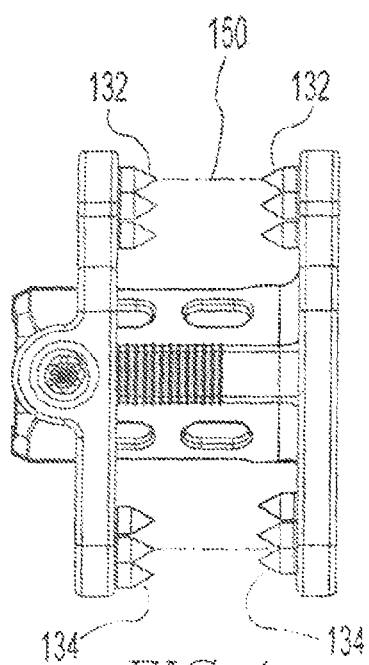
FIG. 4 is a front elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 350. The fasteners 134 at the bottom of the implant 100 are shown offset so that they can interleave if necessary as they are pressed into a bone. Any combination of fastener type, number, and alignment may be provided on the implant 100.

Figure 5:
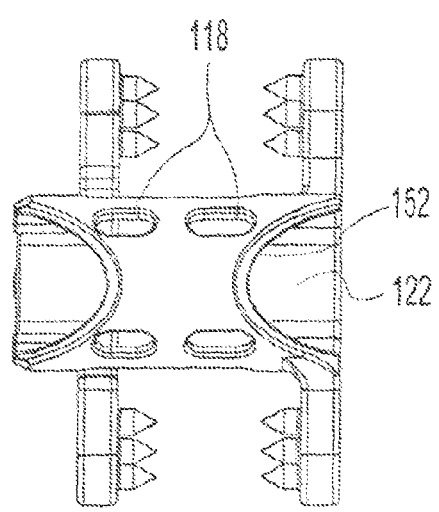
FIG. 5 is a back elevational view of the implant of FIG. 1.
Figure 6:
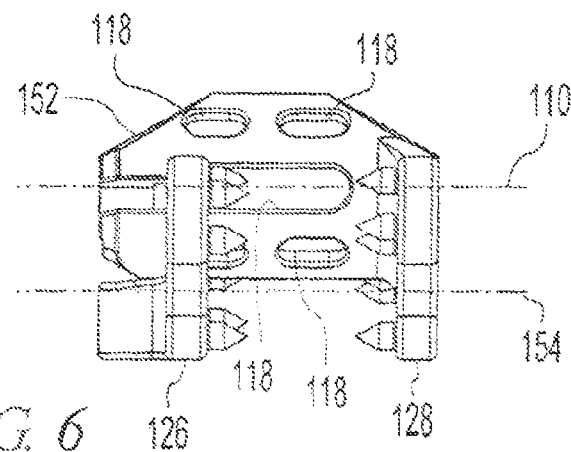
FIG. 6 is a lop plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly relative to the extensions 126, 128 such that the longitudinal axis 110 of the spacer 102 is anterior of the midline 154 of the extensions 126, 128. The anterior offset of the spacer 102 allows it to fit deeply between the spinous processes 20, 21 while the extensions 126, 128 fit alongside the spinous processes 20, 21.

Figure 7:
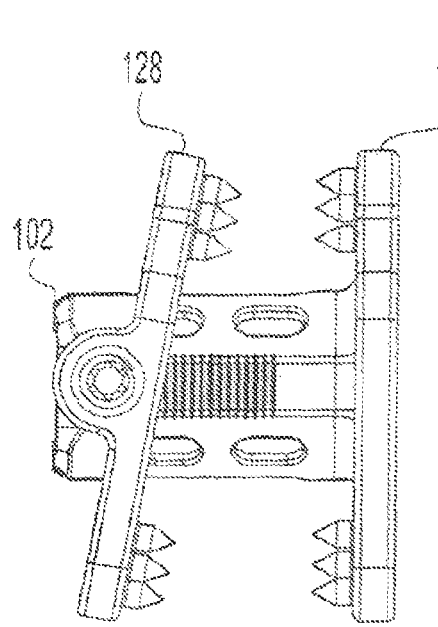
FIG. 7 is a front elevational view of the implant of FIG. 1 showing the assembly in an alternate position.
Figure 8:
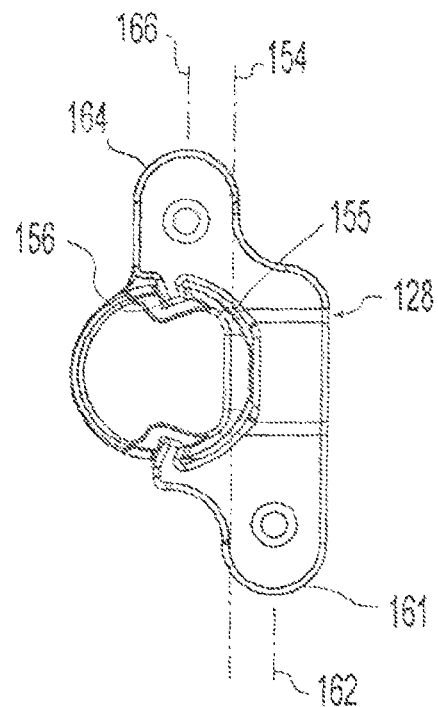
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to positively grip the spacer 102. The aperture 155 may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
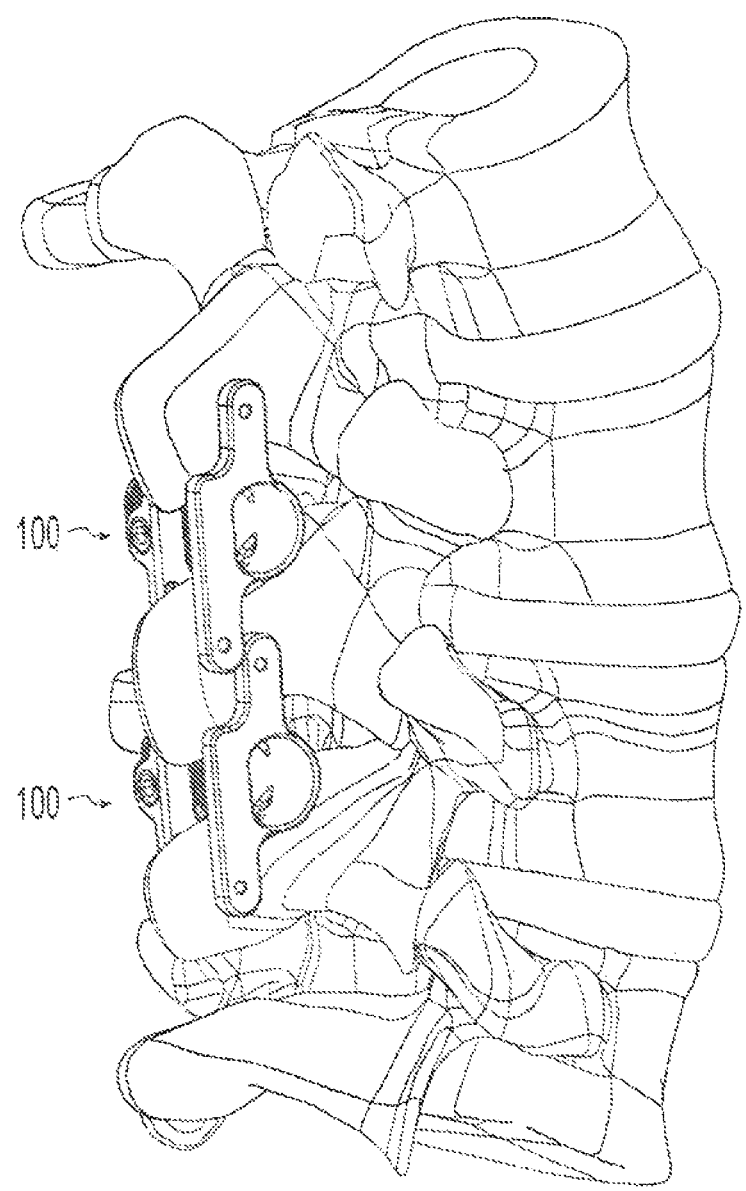
FIG. 9 is a perspective view of a pair of implants like that of FIG. 1 in situ.

As best seen in FIG. 8, the second extension 128 includes a first lobe 161 having a first lobe centerline 162 and a second lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery as shown in FIG. 9 to permit close spacing of the implants, and/or longer extension lobes for more extensive bone engagement. In the illustrative embodiment of FIGS. 1-9, the centerlines 162 and 166 are offset equidistantly from the midline 154 of the second extension 128. The centerlines 162 and 166 may vary from parallel and they may be offset asymmetrically to form different shapes to accommodate different vertebral anatomy. For example, the shape may be tailored for different portions of the spine 10. In the illustrative embodiment of FIGS. 1-9. the first extension 126 has the same shape as the second extension 128. However, the shape may be varied between the first and second extensions 126, 128.

Figure 10:
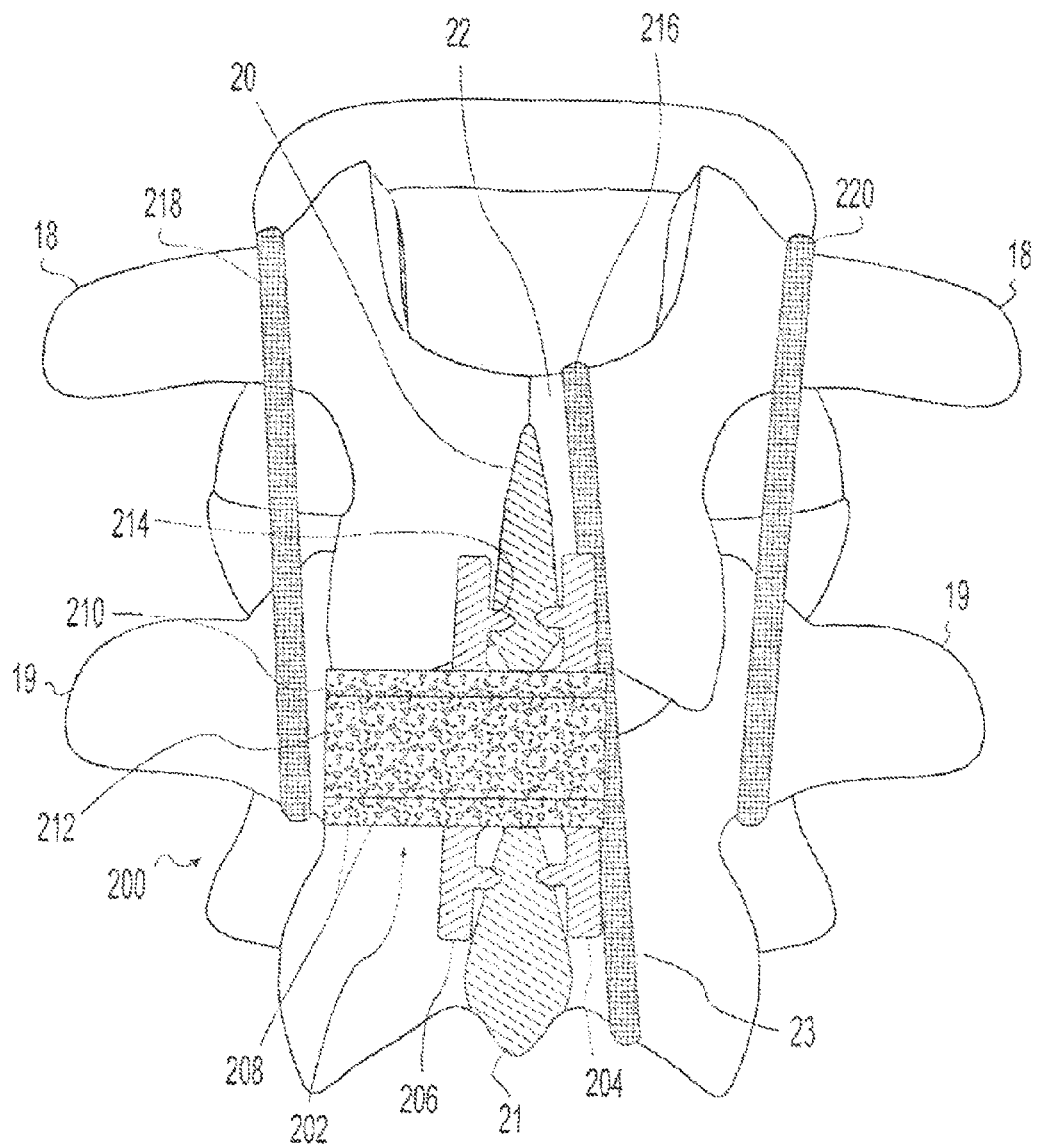
FIG. 10 is across sectional view of an implant like that of FIG. 1 illustrating an alternate material and cerclage elements.

FIG. 10 depicts an implant 200 having a spacer 202 and first and second extensions 204, 206. The spacer 202 includes pores 208 for tissue to grow into. The pores 208 may be individual openings spaced from one another, interconnecting openings, or combinations of individual and interconnecting openings. The spacer 202 may be a monolithic block having uniform porosity throughout. Alternatively, the spacer 202 may include an outer porous layer 210 and an inner layer 212 of different composition. For example, the inner layer 212 may be solid, porous, hollow, or some other configuration. A porous inner layer may have pores of a different size and/or distribution than the outer layer 210. Similarly, any porous portion may have uniform porosity or porosity that varies in pore size or density. A variety of pore configurations are suitable. Preferably the pore size is in the range of 1 µm to 2 mm. More preferably, the pore size is in the range of 1 µm to 500 µm. Still more preferably, the pore size is in the range of 75 µm to 300 µm. The pores may be produced by a variety of processes such as sintering of particles; leaching a soluble component from the material; matting, weaving, or otherwise combining fibers; and/or by any other known process. The pore size may be tailored to preferentially promote hard tissue growth, soft tissue growth, or a combination of hard and soft tissue growth. The extensions 204, 206 may be solid or they may have large and/or small openings to encourage bone growth in and/or around the extensions 204, 206. The spacer 202 and/or extensions 204, 206 may also be coated as previously described.

The extensions 204, 206 may be fixed and/or adjustable. In the illustrative implant 200 of FIG. 10, the first extension 204 is fixed to one end of the spacer 202 and the second extension 206 is translatable along the spacer 202 to allow the extensions to be placed adjacent the spinous processes. The extensions 204, 206 are shown with optional spikes 214 that may engage the spinous processes 20, 21 to fix the spinous processes 20, 21 relative to one another.

FIG. 10 also depicts the use of cerclage in conjunction with the implant 200. For example, one or more flexible bands 216 are placed around the lamina 22, 23 to provide a flexion stop. The band 216 may help carry the load exerted on the spikes 214 during spine flexion. Alternatively or in addition to the band 216, one or more bands 218, 220 may be placed around the transverse processes 18, 19.

Figure 11:
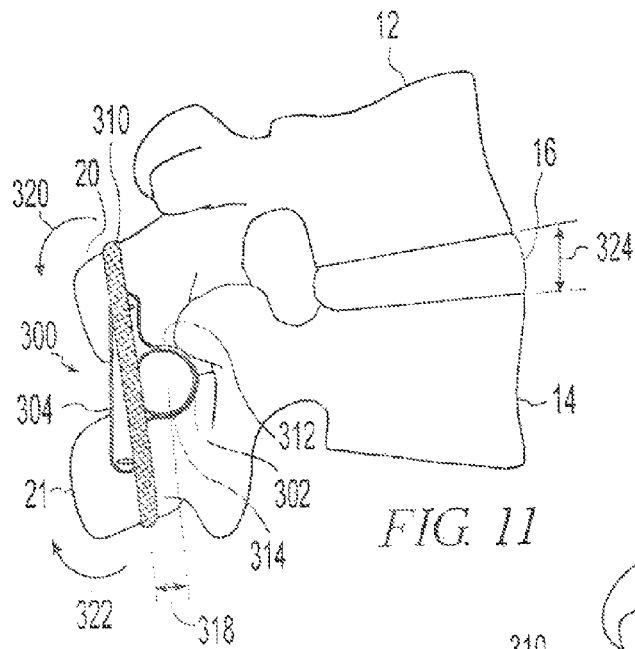
FIGS. 11-13 are side elevational views of an implant like that of FIG. 1 shown in use with cerclage elements.
Figure 12:
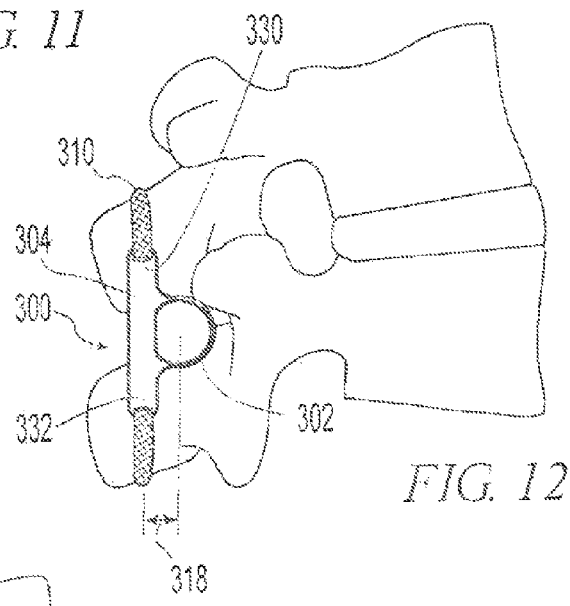
Figure 13:
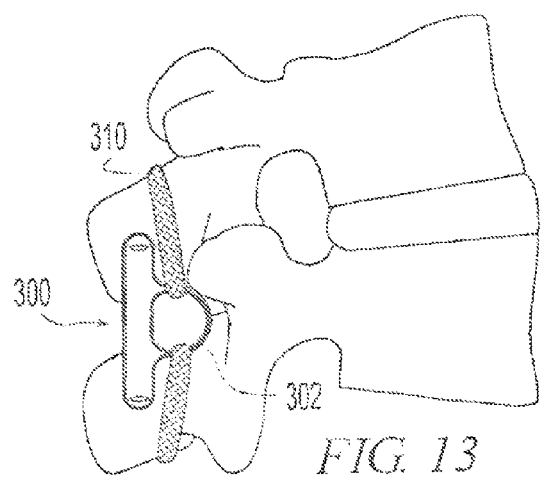

FIGS. 11-13 depict additional examples of the use of cerclage in conjunction with a spinous process implant 300 according to the present invention. The implant includes a spacer 302 for placement between adjacent spinous processes 20, 21 and an extension 304. In the example of FIG. 11, a band 310 of flexible material is looped around the spinous processes 20, 21. By placing the band 310 behind the areas 312, 314 where the spinous processes contact the spacer 302 an offset 318 is created. Tightening of the band 310 creates a moment 320, 322 on each vertebra 12, 14 that offloads some of the pressure on the disc 16 between the adjacent vertebrae 12, 14. With increased tightening of the band 310, the anterior spacing 324 of the vertebrae 12, 14 may actually be increased. Thus, by using the spinous process implant 300 in combination with the band 310, the vertebrae 12, 14 may be levered apart with the implant 300 being used as the fulcrum. In addition to the advantages already mentioned, this combination produces an anterior disc space effect with a posterior spinous process procedure that is less invasive than typical disc spacing procedures.

In the examples of FIGS. 12 and 13, the implant 300 includes a mechanism for attaching the cerclage band 310 to the implant 300. In the example of FIG. 12, the mechanism includes openings 330, 332 in the superior and inferior ends of the extension 304. By attaching the band 310 to the extension 304, the band 310 and extension 304 help stabilize one another against anterior-posterior displacement. This attachment also helps position the band 310 at a predetermined offset 318 from the spacer 302. In the example of FIG. 13, the band 310 is looped through a hollow interior of the spacer 302 itself. In this example, the band is not offset and produces minimal or no moment on the vertebrae.

Figure 14:
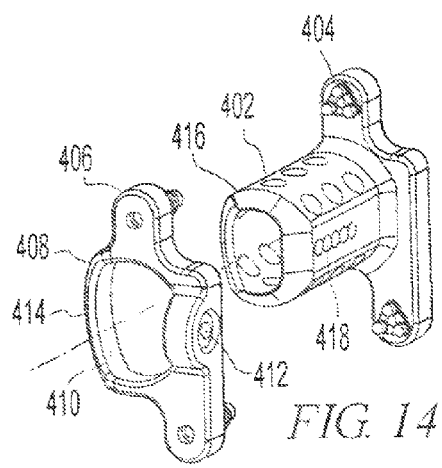
FIGS. 14-24 are perspective views of alternative embodiments of the invention.

FIGS. 14-24 illustrate alternative mechanisms for attaching a movable extension to the implant of FIG. 1. Referring to FIG. 14, an implant 400 includes a spacer 402, a first extension 404 and a second, movable extension 406. The movable extension 406 includes a body in the form of a ring 408 with an inner surface 410 generally conforming to the outer surface of the spacer 402 so that the ring is slidingly receivable on the spacer 402. A set screw 412 is tightened against the spacer 402 to fix the movable extension 406 at a desired position on the spacer 402. Tightening of the set screw 412 biases the movable extension 406 posteriorly relative to the spacer 402. The anterior portion 414 of the ring presses against the anterior portion 416 of the spacer 402 to counter this posterior bias and allow the set screw 412 to lock the extension 406. The spacer 402 may include a plurality of indentations 418 to create a positive engagement with the set screw 412 at predetermined axial locations. The ring 408 may be sized to permit a predetermined amount of tilting of the extension 406 relative to the spacer 402.

Figure 15:
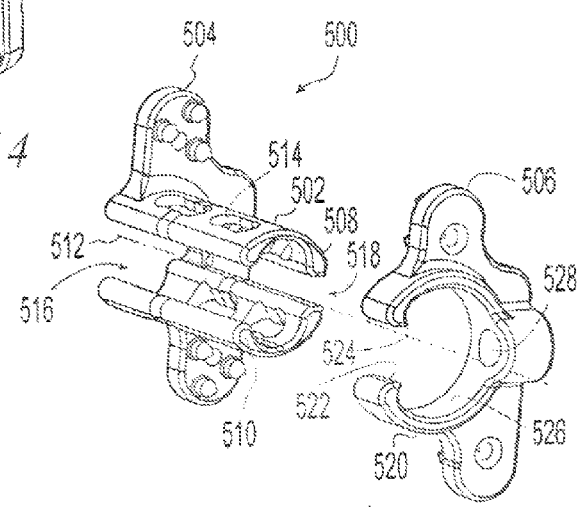

Referring to FIG. 15, an implant 500 includes a spacer 502, a first extension 504, and a second, movable extension 506. The spacer 502 includes a plurality of cantilevered beams 508, 510 projecting parallel so a longitudinal axis 512 away from the first extension 504. In the example of FIG. 15, the spacer 502 includes a pair of opposed "C"-shaped beams 508, 510 with their concave surfaces directed inwardly. The spacer 502 includes openings 514 through the beams 508, 510 and defines elongated openings 516, 518 anteriorly and posteriorly between the beams. The movable extension 506 includes a body in the form of an interrupted ring 520. The ring 520 is open anteriorly and the margins of the opening define posteriorly directed hooks 522, 524. The inner surface 526 of the ring conforms generally to the outer surface of the beams 508, 510 so that the ring is slidingly receivable on the spacer 502. The open anterior configuration of the ring 520 provides clearance to ease sliding of the ring in-vivo. A set screw 528 is tightened against the spacer 502 to fix the movable extension 506 at a desired longitudinal position on the spacer. The hooks 522, 524 curve around a portion of the anterior edge of the beams 508, 510 to resist posterior translation of the ring relative to the spacer 502 when the set screw 528 is tightened.

Figure 16:
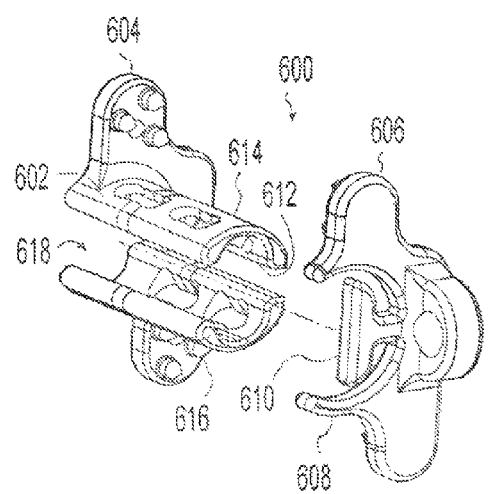

Referring to FIG. 16, an implant 600 is depicted that is similar to implant 500 of FIG. 15 having a spacer 602, first extension 604, and movable extension 606. However, the ring 608 is truncated anteriorly to provide even more anterior clearance than the ring 520 of FIG. 15. The ring 608 includes a key 610 projecting anteriorly from the posterior side of the ring 608 and expanding superiorly and inferiorly to engage the inner surface 612 of the beams 614, 616 to resist posterior translation of the ring relative to the spacer 602. The key 610 also partially blocks the hollow interior 618 of the spacer 602 to help retain material optionally packed into the interior 618.

Figure 17:
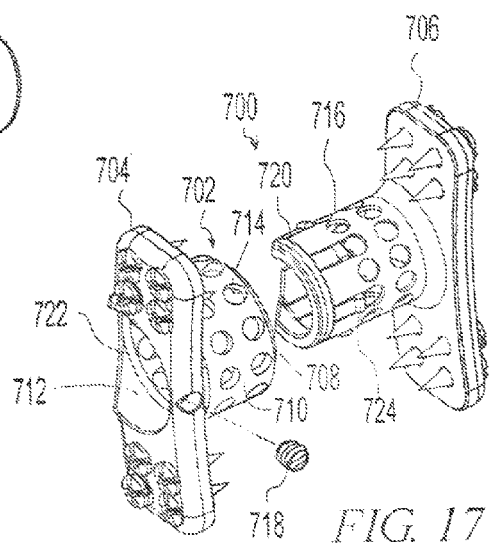

Referring to FIG. 17, an implant 700 includes a spacer 702, a first extension 704, and a second movable extension 706. The spacer 702 includes a sidewall 708 defining an outer surface 710 and an inner surface 712. In the example of FIG. 17, the spacer 702 is generally in the shape of a hollow flattened cylinder with a "D"-shaped cross section. However, the spacer 702 could be any desirable shape. The spacer 702 includes a plurality of openings 714 communicating from the outer surface 710 to the inner surface 712. The movable extension 706 includes a projection 716 configured generally like the spacer 702 but being sized to slide within the spacer 702 in telescoping relationship. The projection (or the spacer) may optionally include one or more fixation mechanisms to lock the extensions 704, 706 at a desired longitudinal spacing. Fixation mechanisms may include a set screw 718, a ndge 720 forming a snap fit with a groove 722 or other feature, a detent 724 engageable with openings 714, and/or other suitable fixation mechanisms. Any one or combinations of these mechanisms may be used and they may be reversed from the orientation shown.

Figure 18:
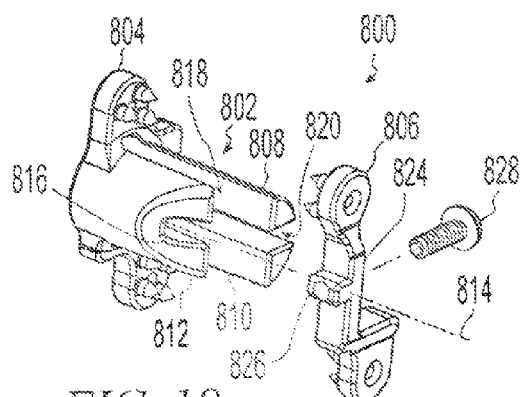
Figure 19:
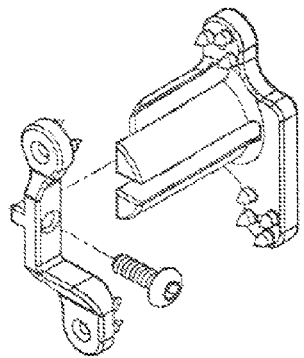
Figure 20:
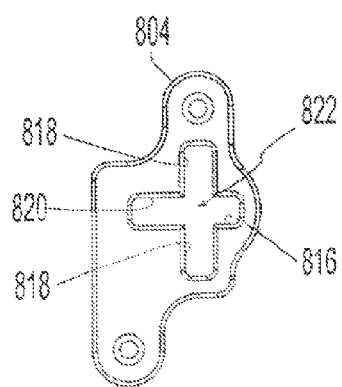

Referring to FIGS. 18-20, an implant 800 includes a spacer 802, a first extension 804, and a second, movable extension 806. The spacer 802 includes a plurality of cantilevered beams similar to FIGS. 15 and 16 except that in this example there are three beams 808, 810, 812. The beams project parallel to a longitudinal axis 814 away from the first extension 804. In the example of FIG. 18, the anterior beam 812 includes a posteriorly opening groove 816. The posterior beams 808, 810 and anterior beam 812 define an elongated slot 818 between them opening superiorly and inferiorly. The posterior beams 808, 810 further define an elongated slot 820 between them opening posteriorly. FIG. 20 illustrates a cruciform opening 822 defined by the projection of the groove 816 and slots 818, 820 projected through the first extension 804. The movable extension 806 includes a body 824 sized to slidingly engage the slot 818. An optional lug 826 can project anteriorly into groove 816 to constrain tilting of the movable extension 806 relative to the first extension 804. The lug 826 can be sized to fit closely within groove 816 to prevent tilting of the movable extension 806 or it cart be sized smaller than the groove 816 to permit a predetermined amount of tilt. A set screw 828 is provided to lock the movable extension 806 to the spacer 802.

Figure 21:
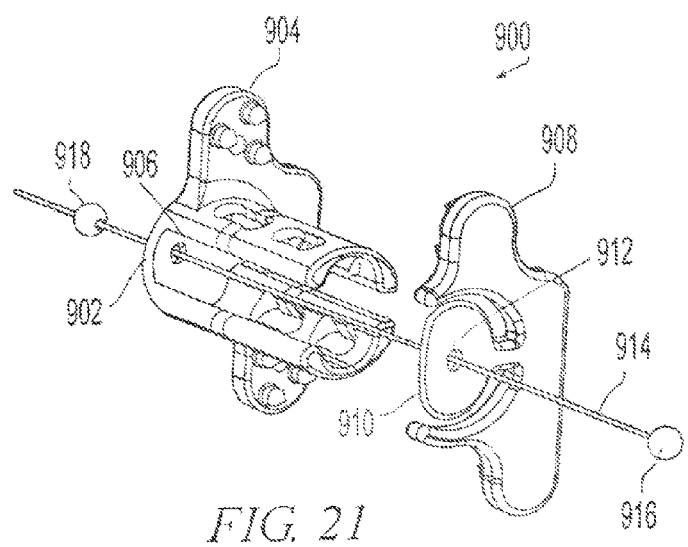

Referring to FIG. 21, an implant 900 is depicted that is configured generally like that of FIG. 16. However, an end wall 902 adjacent the first extension 904 includes a through bore 906 and the movable extension 908 includes a key 910 with a through bore 912. The bores 906, 912 receive a fastener to fix the extensions 904, 908 at a maximum spacing to prevent them from moving apart. Fasteners may include screws, bolts, nuts, cables, wires, ties, rods, and/or any other suitable fastener. In the example of FIG. 21, the fastener includes an elongated crimp receiving member 914, such as a cable, and crimp members 916, 918, such as ferrules or compressible beads.

Figure 22:
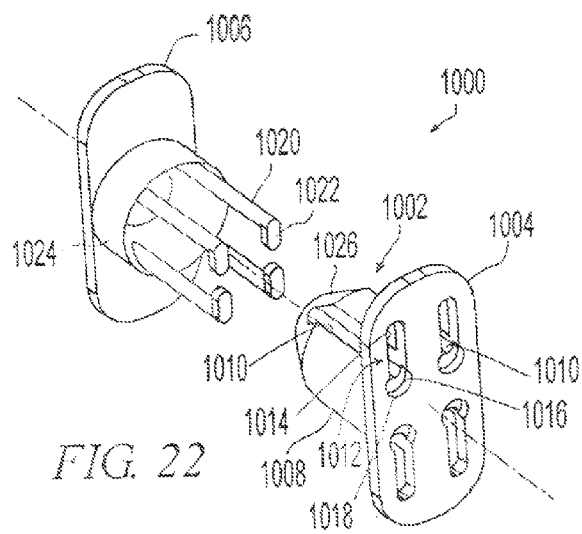

Referring to FIG. 22, an implant 1000 includes a spacer 1002, a first extension 1004, and a second extension 1006. The spacer 1002 includes an outer surface 1008 defining one or more longitudinal grooves 1010 extending along the outer surface 1008 and through the first extension 1004. The first extension 1004 includes one or more corresponding slots 1012 having a radially outwardly extending portion 1014 through the first extension 1004 and communicating with the grooves 1010. The slots 1012 have a radially inwardly extending portion 1016 defining a shoulder 1018 at the end of the grooves 1010. The second extension 1006 includes one or more corresponding projections 1020 projecting longitudinally toward the first extension 1004 and terminating at a radially inwardly directed tab 1022. The second extension 1006 further includes a centering bore 1024 having conical opening engageable with a conical free end 1026 of the spacer 1002. The second extension 1006 is attached to the spacer 1002 by pressing the tabs 1022 against the conical end 1026 of the spacer 1002 to spread the projections outwardly until the labs 1022 engage the grooves 1010. The tabs 1022 are slid along the grooves 1010 until they exit through the slots 1012 and the tabs 1022 snap inwardly over the shoulders 1018 and into the portions 1016. Abutment of the tabs 1022 against the shoulders 1018 prevents the first and second extensions 1004, 1006 from moving apart. The engagement of the conical end 1026 of the spacer 1002 with the bore 1024 provides radial stability to the assembly.

Figure 23:
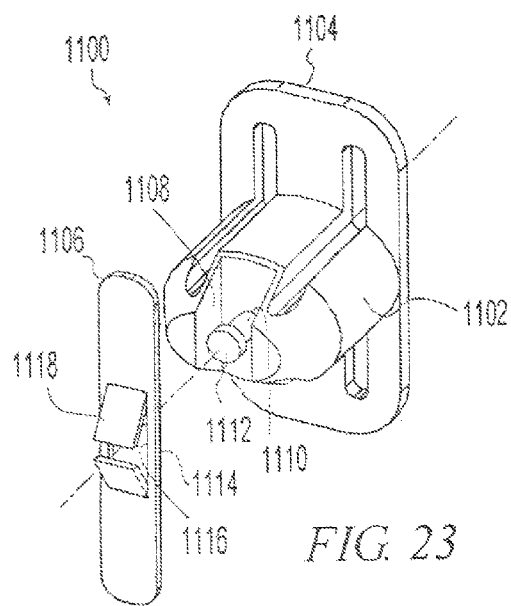

Referring to FIG. 23, an implant 1100 includes a spacer 1102, a first extension 1104, and a second extension 1106. The spacer 1102 includes a transverse groove 1108 with a central boss 1110 having an enlarged head 1112. The second extension 1106 includes a portion 1114 sized to fit within the groove 1108 and an opening 1116 bordered by one or more angled tabs 1118. The second extension 1112 is assembled to the spacer by pressing the portion 1114 into the groove 1108 with the central boss 1110 directed into the opening 1116. As the boss 1110 is pressed through the opening 1116, the tabs 1118 flex outwardly to allow it to pass. Once the boss 1110 is past the tabs 1118, the tabs 1118 return to their original position and snap behind the enlarged head 1112. In this configuration, the boss 1110 retains the second extension 1106 longitudinally and the groove 1108 prevents the second extension 1106 from rotating about the longitudinal axis of the implant 1100.

Figure 24:
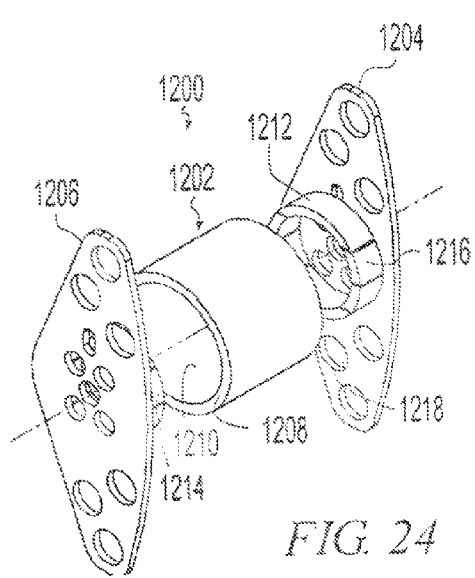

Referring to FIG. 24, an implant 1200 includes a spacer 1202, a first extension 1204, and a second extension 1206. The spacer 1202 includes a solid cylindrical sidewall 1208 defining a hollow interior 1210. The extensions 1204, 1206 are similarly configured and each includes a projection 1212, 1214 sized to fit inside of the spacer 1202. The extensions 1204, 1206 may attach to the spacer by press-fitting, snap-fitting, screwing, and/or otherwise engaging the projections 1212, 1214 with the spacer 1202. Alternatively, or additionally, the extensions 1204, 1206 may attach to the spacer 1202 with any of the previously depicted attachment mechanisms such as with a setscrew as shown in FIG. 3 or an elongated fastener as shown in FIG. 21. In the example of FIG. 24, the extensions 1204, 1206 are slotted longitudinally to form flexible petals 1216 that press into the spacer 1202. The extensions 1204, 1206 include openings 1218 to allow tissue growth, permit attachment of cerclage members, and/or receive additional fasteners attached to the spinous processes.

The spacer 1202 of FIG. 24 could have openings as shown in some of the other examples. Likewise, the other examples could have a solid surface as shown in FIG. 24. Similarly the extensions of any of the examples may be solid, have openings, or be otherwise advantageously configured.

Implants according to the present invention may be implanted using a variety of surgical approaches and techniques. Surgical approaches may include superspinous ligament sacrificing posterior approaches, superspinous ligament preserving posterior approaches, lateral approaches, and/or other suitable approaches. Techniques may include leaving the tissues at the surgical site unmodified or modifying the tissues such as trimming, rasping, roughening, and/or otherwise modifying them. For example, in FIG. 1, a lateral approach is used and the inferior spinous process is cut on its superior surface 26 to enlarge the interspinous space to receive the implant 100. After the interspinous space is prepared, the spacer 102 is inserted into the interspinous space. If a first extension 126 is present it may be pressed inwardly to lie near or abut one or more spinous processes. If a second extension 128 is used, it is engaged with the spacer 102 and also optionally pressed inwardly. In FIG. 1, opposing extensions 126, 128 having inwardly directed bone fasteners have been used and pressed inwardly so that the fasteners 132 engage the spinous processes 20, 21. The engagement of the fasteners 132 with the inferior spinous process 21 is not shown in FIG. 1 because the extensions are offset superiorly and inferiorly as shown in FIGS. 3, 8, and 9.

Figure 25:
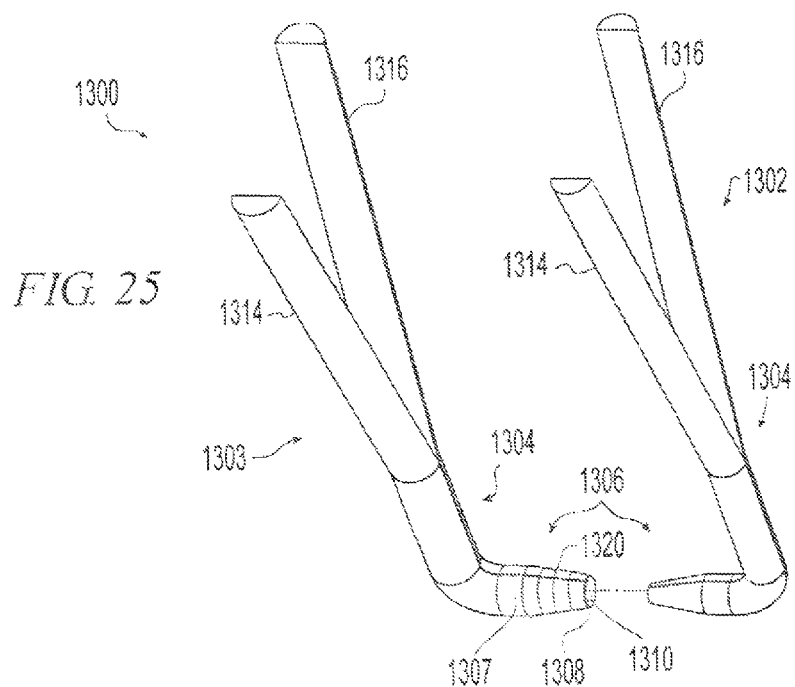
FIG. 25 is a perspective view of instrumentation for implanting the implant of FIG. 1.
Figure 26:
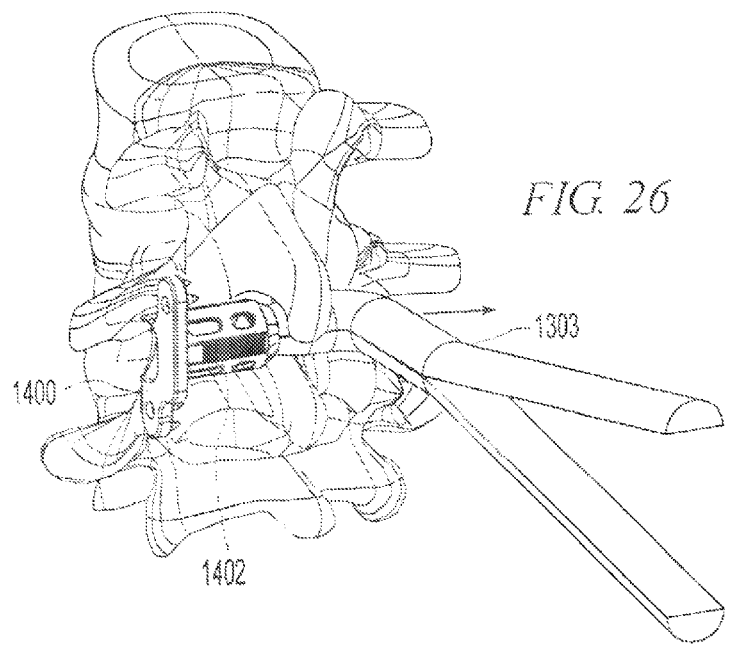
FIG. 26 is a perspective view of the instrumentation of FIG. 25 in use to implant the implant of FIG. 1.

Referring to FIGS. 25 and 26, a set of instruments 1300 is provided to facilitate lateral insertion of an implant into the interspinous space. The set of instruments includes a plurality of inserters 1302, 1303 in which each inserter 1302, 1303 has a first or handle portion 1304 and a second or working portion 1306. The working portion 1306 is insertable into the interspinous space. Preferably, the handle portion 1304 extends transverse to the working portion 1306 to facilitate holding and manipulating the inserter 1302, 1303 while the working portion 1306 is in the interspinous space. The handle portion 1304 and working portion 1306 may define a curve, angle, offset, and/or any other suitable transverse orientation. In the example of FIG. 25, the inserters 1302, 1303 are generally "L"-shaped. The working portion 1306 tapers from a relatively larger cross-sectional dimension at a first portion 1307 spaced away from its free end 1308 to a relatively smaller cross-sectional dimension at its free end 1308. In the illustrative embodiment, the working portion is conical and tapers from a larger diameter to a smaller diameter. The end 1308 defines a hollow tip having an opening 1310. The set of instruments 1300 is provided with a plurality of similarly configured inserters having differently sized working portions 1306 such that the end 1308 of one inserter 1302 will fit inside the opening 1310 at the tip of another inserter 1303. Optionally, the working portion 1306 may be separated into opposing halves attached to opposing handles 1314, 1316. As the opposing handles 1314, 1316 are moved relative to one another, the opposing halves of the working portion 1306 move relative to one another. In the illustrative embodiment, squeezing the handles 1314, 1316 toward one another causes the working portion 1306 to expand as the opposing halves of the working portion 1306 open outwardly away from one another.

In use, a first inserter 1302 is inserted into the interspinous space. The first inserter 1302 is relatively small to ease insertion. As the end 1308 is inserted further, the tapered working portion 1306 expands the interspinous space. Optionally, the interspinous space can be further expanded by expanding the working portion while it is inside the interspinous space such as by squeezing the handles 1314, 1316. A second, larger inserter 1302 is engaged with the first inserter 1303 by placing its hollow tip over the tip of the first inserter 1303 and then passing the overlapping instruments back through the interspinous space to remove the first inserter 1303 and insert the second inserter 1302. As the end of the second inserter 1303 is inserted further, the tapered working portion expands the interspinous space. Optionally, the interspinous space can be further expanded by expanding the working portion while it is inside the interspinous space. Progressively larger inserters can be inserted in this fashion until the interspinous space has been expanded to the desired size. Once the desired size has been reached the appropriate implant size may be determined by noting the size of the last inserter. The inserter may optionally include indicia 1320 on the tapered working end corresponding to different spacer sizes to further facilitate sizing the implant. The implant is inserted by engaging the spacer 1402 with the working end of the inserter as shown in FIG. 26. The implant may be engaged inside of the hollow tip of the inserter or the tip of the inserter may engage a hollow tip on the implant as shown. The spacer 1402 is pressed into the interspinous space as the inserter is withdrawn.

Figure 27:
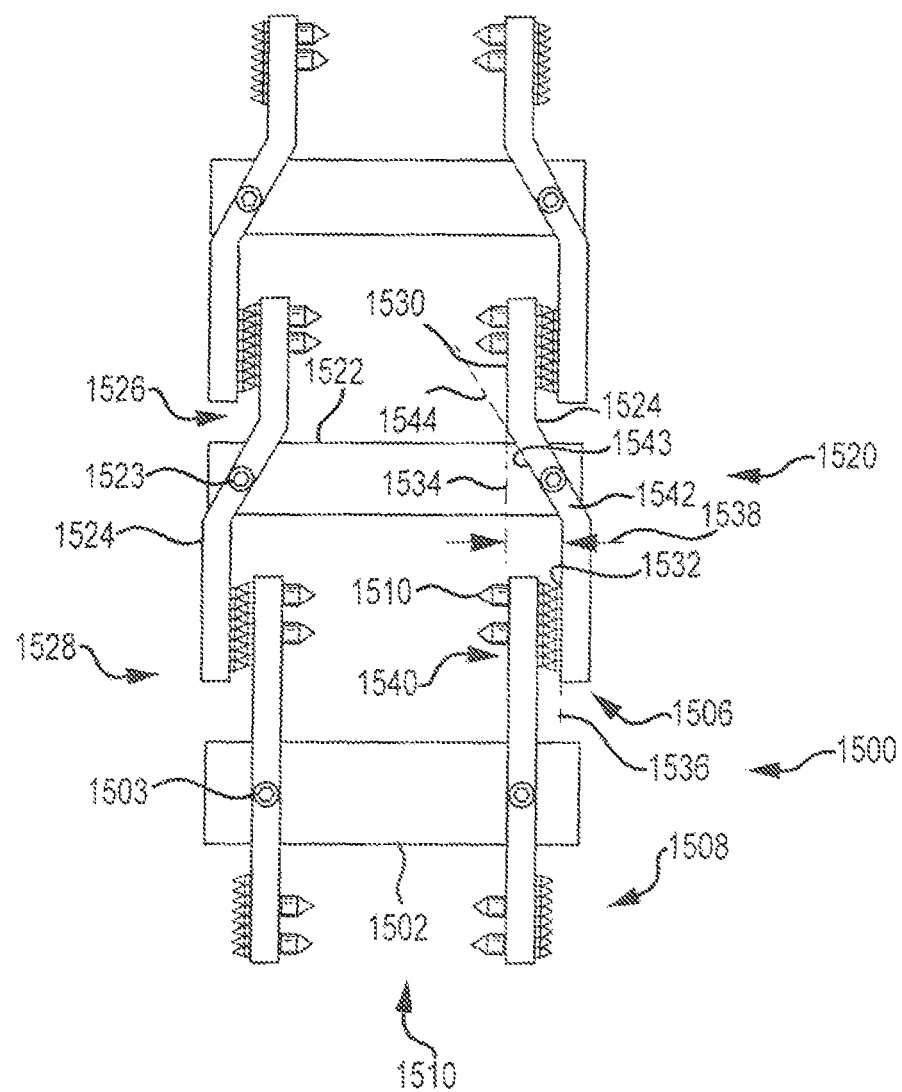
FIG. 27-58 are perspective views of aspects of the invention.
Figure 28:
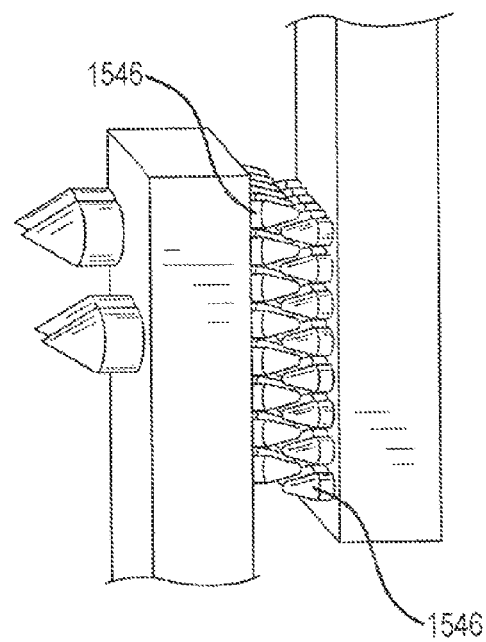

Referring to FIGS. 27-28, a first implant 1500 includes a spacer 1502 and extensions 1504. The extensions are generally planar in the anterior-posterior plane as shown in FIG. 27, and include a superior portion 1506, an inferior portion 1508, and spikes 1510 projecting medially from each of the superior and inferior portions to engage spinous processes superior and inferior to the spacer 1502. The extensions 1504 are mounted to the spacer 1502 to permit the spacing between the extensions to be adjusted such as by surrounding and sliding along a portion of the spacer 1502 and to permit the spacing between the extensions to be locked such as with set screw 1503. A second implant 1520 includes a spacer 1522, extensions 1524, and set screw 1523. The extensions 1524 include a superior portion 1526 and an inferior portion 1528. The inferior portion 1528 is offset laterally (outwardly) relative to the superior portion 1526 to facilitate the inferior portion 1528 overlying the superior portion 1506 of the first implant 1500 in a shingle-like arrangement. In the illustrative example, the superior portion 1526 and inferior portion 1528 define medial surfaces 1530, 1532 lying generally in planes 1534, 1536 that are generally parallel to one another and offset by a distance 1538. The distance 1538 is preferably equal to at least the thickness 1540 of the superior portion 1506 of the first implant to allow the inferior portion 1528 of the extension 1524 to lie flat against the superior portion 1506 of the extension 1504. The offset distance 1538 may be other values that result in an angular engagement of the inferior portion 1528 of the extension 1524 with the superior portion 1506 of the extension 1504. The offset may be defined by a discreet offset portion 1542 shown as a generally straight portion defining a medial surface 1543 lying generally in a plane 1544 transverse to planes 1534 and 1536. Alternatively, any one or combination of portions 1526, 1528, and 1544, including surfaces 1530, 1532, and 1543 may be flat, curved, or otherwise shaped. Likewise, the offset may be reversed so that the extensions of first implant 1500 overlie the extensions of second implant 1520.

Figure 29:
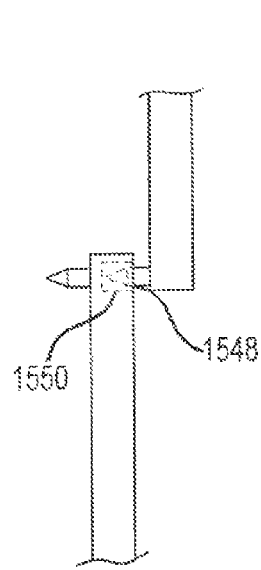

Preferably, the inferior portion 1528 of extension 1524 includes a medially feeing gripping feature and the superior portion 1506 of extension 1504 includes a cooperating laterally facing gripping surface. In the illustrative example of FIG. 27, shown more clearly in FIG. 28, the gripping surfaces include a plurality of conical bristles 1546 able to nest together to resist relative sliding between the extensions 1504, 1524. FIG. 29 illustrates an alternative arrangement in which a spike 1548 from one extension engages a hole 1550 in another extension.

In use, the first implant is placed with its spacer between adjacent spinous processes at a first spinal level and the spikes of its extensions engaging the sides of the adjacent spinous processes. A second implant is then placed with its spacer between adjacent spinous processes at a second spinal level and the spikes at one end of its extensions engaging the sides of a spinous process and the other end overlying and engaging the extensions of the first implant.

Figure 30:
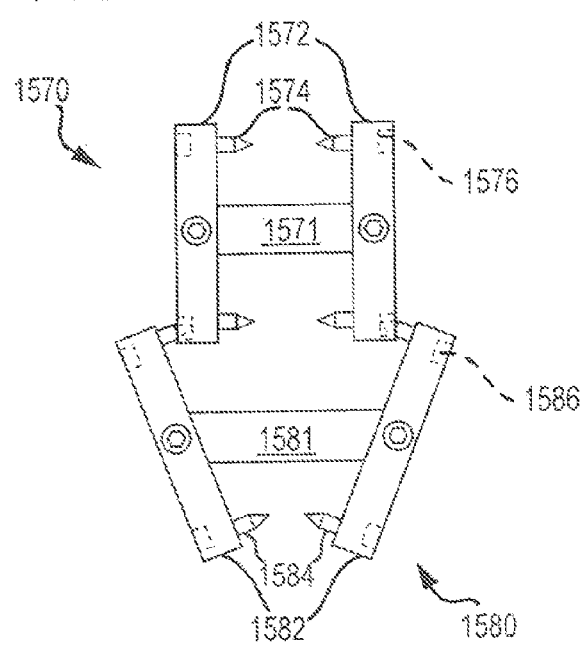
Figure 31:
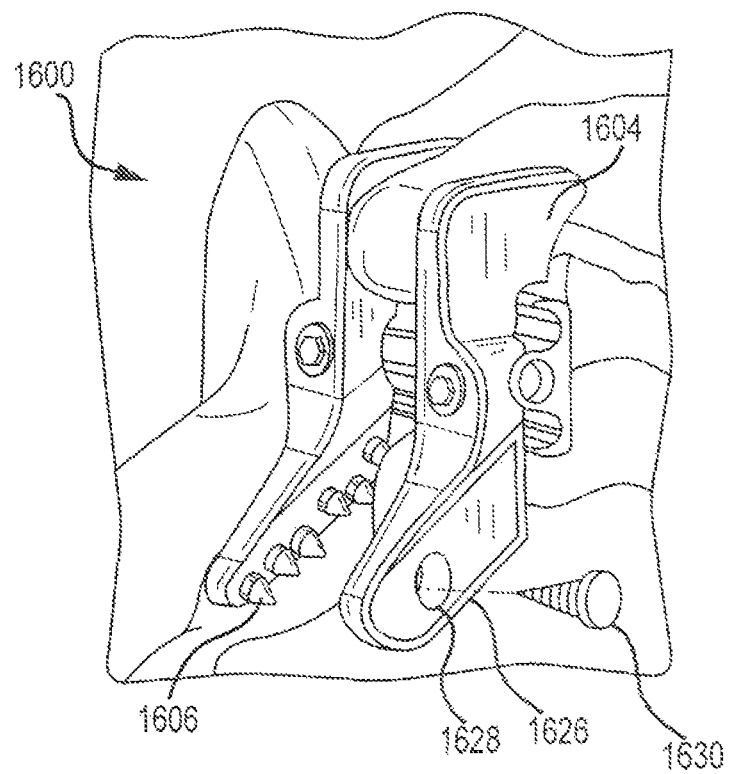
Figure 32:
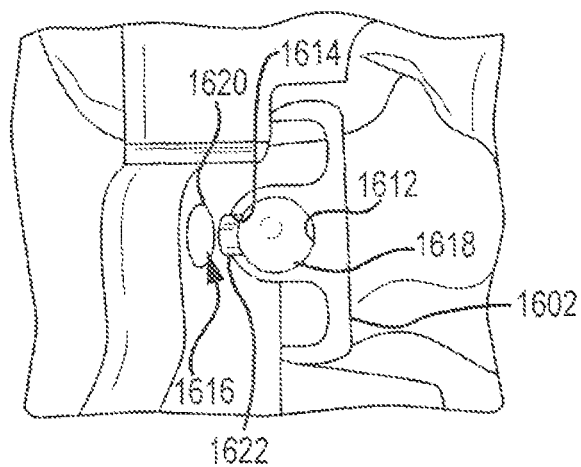
Figure 33:
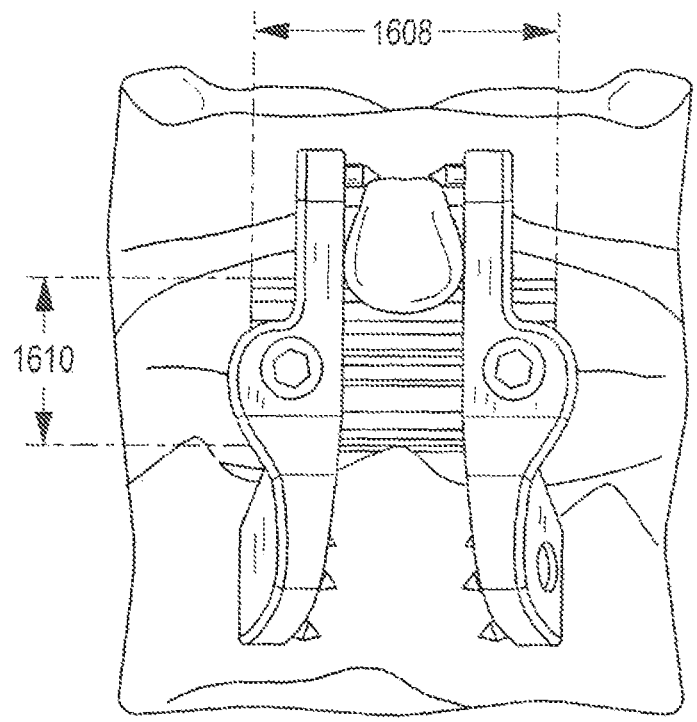
Figure 34:
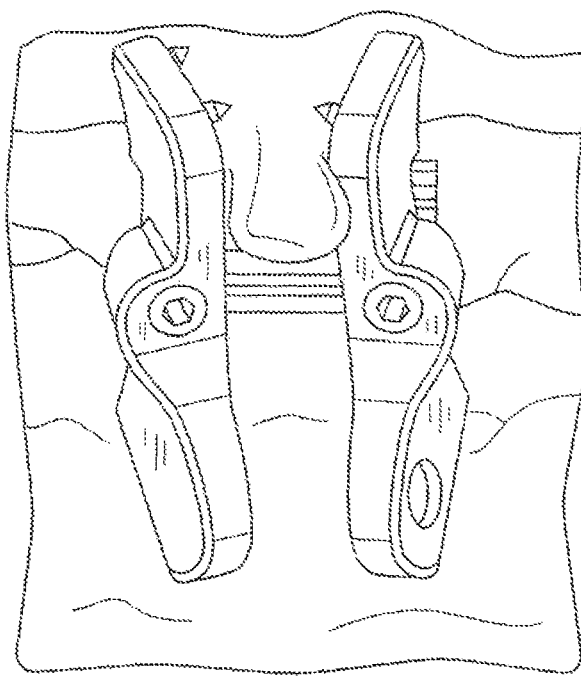

Referring to FIG. 30, two implants 1570, 1580 are shown in overlapping relationship. Implant 1570 includes a spacer 1571 and generally planar extensions 1572 having medially facing spikes 1574 and laterally facing sockets 1576. The extensions 1572 are able to engage the spacer 1571 at variable angles. Implant 1580 likewise includes a spacer 1581 and generally planar extensions 1582 having medially facing spikes 1584 and laterally facing sockets 1586. The extensions 1582 are able to engage the spacer 1581 at variable angles. The spikes of the extensions of one implant are receivable in the sockets of the extensions of another implant at varying angles from coaxial, or parallel, to angles as high as 45 degrees or higher. In use, one implant is placed with its spacer between adjacent spinous processes at a first spinal level and the spikes of its extensions engaging the sides of the adjacent spinous processes. A second implant is then placed with its spacer between adjacent spinous processes at a second spinal level and the spikes at one end of its extensions engaging the sides of a spinous process and the spikes at another end of its extensions engaging sockets in the extensions of the first placed implant.

In the illustrative example of FIG. 30, no offset is required in the extensions to permit an overlying relationship due to the variable angle between the extensions and the spacers. The implants of FIG. 27 may likewise permit variable angles between extensions and spacers. However, because of the offset of the extensions, the extensions will assume a more parallel orientation. The implants of FIGS. 27-30 may incorporate features of any of the plurality of implants described throughout this specification.

The above described overlying implants facilitate placement of implants at adjacent spine levels by permitting the extensions to overlap and thus the extensions require less space on the sides of the spinous processes. In addition, where a rigid connection is formed between overlapping extensions, the rigidity of the overall spinal construct of multiple implants is increases. In the above described overlying implants, opposing surfaces of overlapping extensions may include pads, hooks, pins, teeth, bristles, surface roughness, adhesive, holes, loops, screws, bolts, and/or other features that permit one extension to grip another.

Referring to FIGS. 31-34. an implant 1600 includes a spacer 1602 and extensions 1604. The extensions 1604 include medially facing spikes 1606 for engaging the vertebrae. The spacer 1602 has a length 1608 extending medially-laterally and a height 1610 extending superiorly-inferiorly. A cylindrical path 1612 extends through the spacer 1602 along its length. The cylindrical path 1612 opens posteriorly through a slot 1614. A draw bolt 1616 has a spherical tip 1618 at a first end and a cylindrical threaded portion 1620 at a second, opposite end. The tip 1618 and threaded portion are connected by a neck 1622. The extensions 1604 include threaded bores 1624 formed through the extensions 1604 in an anterior-posterior direction. The implant 1600 is assembled by threading the draw boll 1616 into the extensions 1604 with the tip 1618 projecting anteriorly. The tip is slidingly engaged with the path 1612 in the spacer 1602 with the neck projecting through the slot 1614.

In use, the spacer 1602 is placed between adjacent spinous processes and the extensions 1604 are engaged with the spacer 1602. Alternatively, one or both extensions 1604 may be preassembled to the spacer before the spacer 1602 is inserted between adjacent spinous processes. The extensions 1604 are pressed together to engage the spikes 1606 with the spinous processes. The fit of the spherical tip 1618 of the draw bolt 1616 within the cylindrical path 1612 permits the extensions 1604 to be angled relative to the spacer 1602. If the neck 1622 of the draw bolt 1616 fits closely within the slot 1614, the extensions are constrained to angulate medially-laterally. IF the neck 1622 of the draw bolt 1616 fits loosely within the slot 1614, the extensions may angle both medially-laterally and superiorly-inferiorly. The angulation of the extensions permits them to adjust to the angle of the underlying bone. Each draw bolt 1616 is then rotated to move the corresponding extension 1604 toward the spacer 1602 until the extension 1604 abuts the spacer 1602. Further rotation of the draw bolt presses the extension 1604 and spacer 1602 together to lock their relative positions.

In the illustrative example of FIGS. 31-34, the extensions 1604 are flared outwardly at an inferior portion 1626. This outward flare directs the superior spikes outwardly and inwardly to accommodate a small or missing spinous process such as, for example, on the sacrum of a patient. The inferior portion may include one or more holes 1628 to receive screws 1630 that seat on the inferior portion and engage the inferior vertebra, such as, for example, the sacrum to more positively engage the inferior vertebra.

Figure 35:
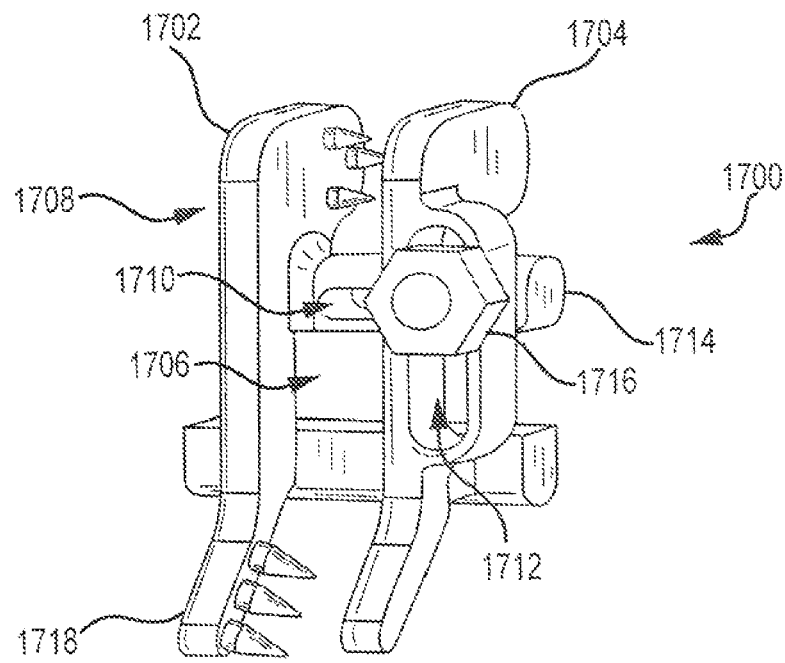
Figure 36:
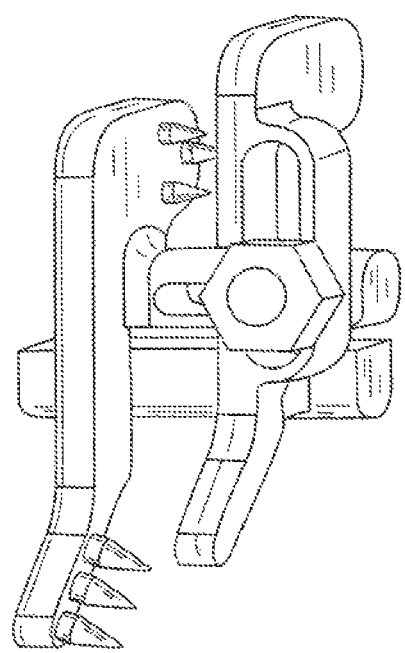

Referring to FIGS. 35-36, an implant 1700 includes a first half 1702 and a second half 1704. Each half 1702, 1704 includes both a portion of a spacer 1706 and an extension 1708. At least one of the spacer portions includes a medial-lateral slot 1710 and at least one of the extensions includes a superior-inferior slot 1712. When assembled, the slots 1710, 1712 overlie one another and a bolt 1714 extends through the slots to pin the first and second halves 1702, 1704 together. A nut 1716 captures the bolt 1714. The superior-inferior slot 1712 permits adjustment of the superior-inferior spacing between the spacer portions 1706 to vary the spacer height as can be seen by comparing FIGS. 35 and 36. The medial-lateral slot 1710 permits adjustment of the medial-lateral spacing between the extensions 1708 to allow the extensions to be engaged with the spinous processes. When the desired spacings are achieved, the nut 1716 is tightened to compress the assembly together and simultaneously lock both of the spacings. In the illustrative example of FIGS. 35-36, the inferior portion 1718 of at least one of the extensions has angled spikes arranged to engage an inferior vertebra with a small or missing spinous process such as the sacrum. In this example, one extension has spikes superiorly and inferiorly while the other extension is smooth to ease height adjustment.

Figure 37:
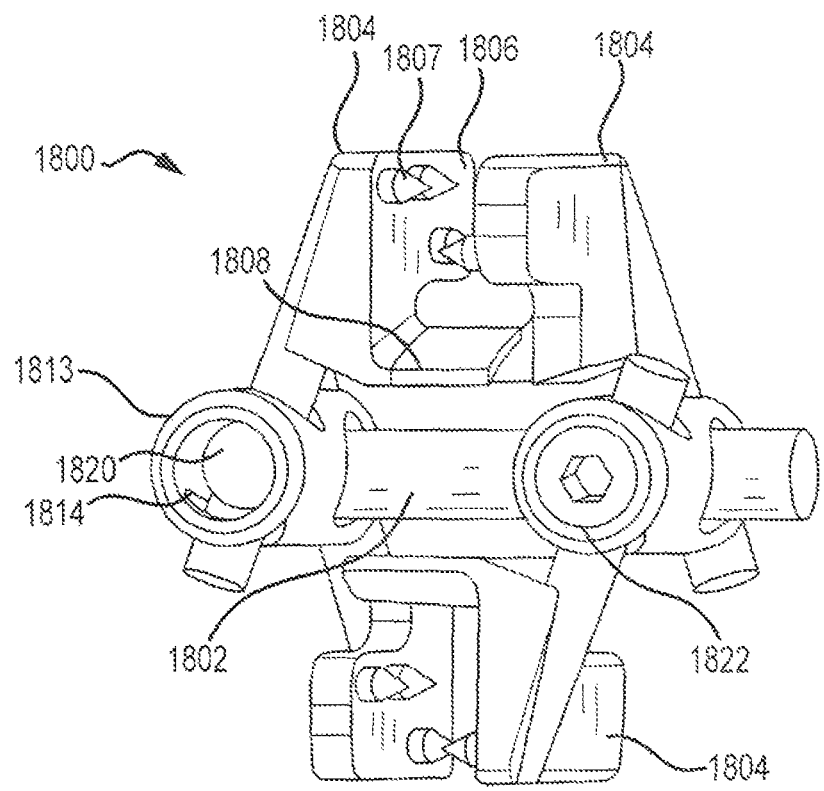
Figure 38:
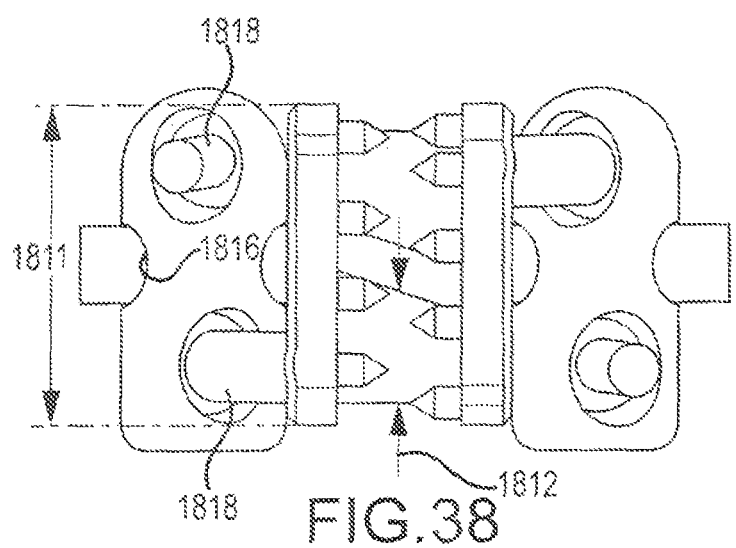

Referring to FIGS. 37-38, a modular implant 1800 includes a cross bar 1802 and extensions 1804. Each extension 1804 includes a spiked pad 1806 with spikes 1807 projecting outwardly from the spiked pad, a spinous process shelf 1808 projecting outwardly in the same direction as the spikes 1807, and an extension rod 1810. The spiked pad 1806 has a width 1811 and the spinous process shelf 1808 has a width 1812. In the illustrative example of FIGS. 37-38, the spinous process shelf width 1812 is less than the spiked pad width 1811 to permit assembly of aligned, opposing extensions 1804 with spinous process shelves 1808 lying side-by-side in the same plane. Further, in the illustrative example of FIGS. 37-38, the spinous process shelf width 1812 is less than one-half the spiked pad width 1811 to permit assembly of aligned, opposing extensions 1804 with spinous process shelves 1808 lying side-by-side in the same plane with a gap between them to permit tissue growth between the shelves. A joint cylinder 1813 includes a threaded axial bore 1814 along the longitudinal axis of the joint cylinder and multiple transverse bores transverse to the axial bore 1814 and extending through the joint cylinder 1813 sidewall. The transverse bores include an inboard transverse bore 1816 and outboard transverse bores 1818 on either side of the inboard transverse bore 1816. The inboard transverse bore 1816 is sized to receive the cross bar 1802 in close fitting sliding relationship. The outboard transverse bores 1818 are sized to receive the extension rods 1810 loosely to permit the extension rods 1810 to toggle in the bores.

The modular implant 1800 is assembled by placing a joint cylinder 1813 on each end of a cross bar 1802 with the cross bar 1802 extending through the inboard bore 1816 of each joint cylinder 1813. Two cross-drilled balls 1820 are next inserted into the axial bore 1814 of each joint cylinder 1813 and aligned with the outboard bores 1818 Two extensions are mounted to each joint cylinder 1813 by inserting the extension rod 1810 of each extension into the outboard bores 1818 and through the corresponding cross-drilled ball 1820. The cross-drilled balls 1820 are sized so fit closely within the axial bore 1814 and touch the cross bar 1802. Once assembled, the modular implant 1800 can be adjusted by sliding and rotating the joint cylinders 1813 relative to the cross bar 1802 and sliding, rotating, and toggling the extension rods 1810 relative to the joint cylinders 1813. When the desired adjustment is achieved, a set screw 1822 is inserted into at least one side of each axial bore 1814 and tightened to compress the cross-drilled bails 1820, extension rods 1810, and cross bar 1802 tightly together and thereby lock the adjustment. In the illustrative example of FIGS. 37-38, the extensions 1804 are all identical, the cross-drilled balls are identical, and the joint cylinders are identical so that an implant can be assembled from a few basic components simplifying assembly and reducing inventory costs. However, if desired, a wider variety of component shapes and sizes may be provided to allow the modular implant to be tailored in various ways.

Figure 39:
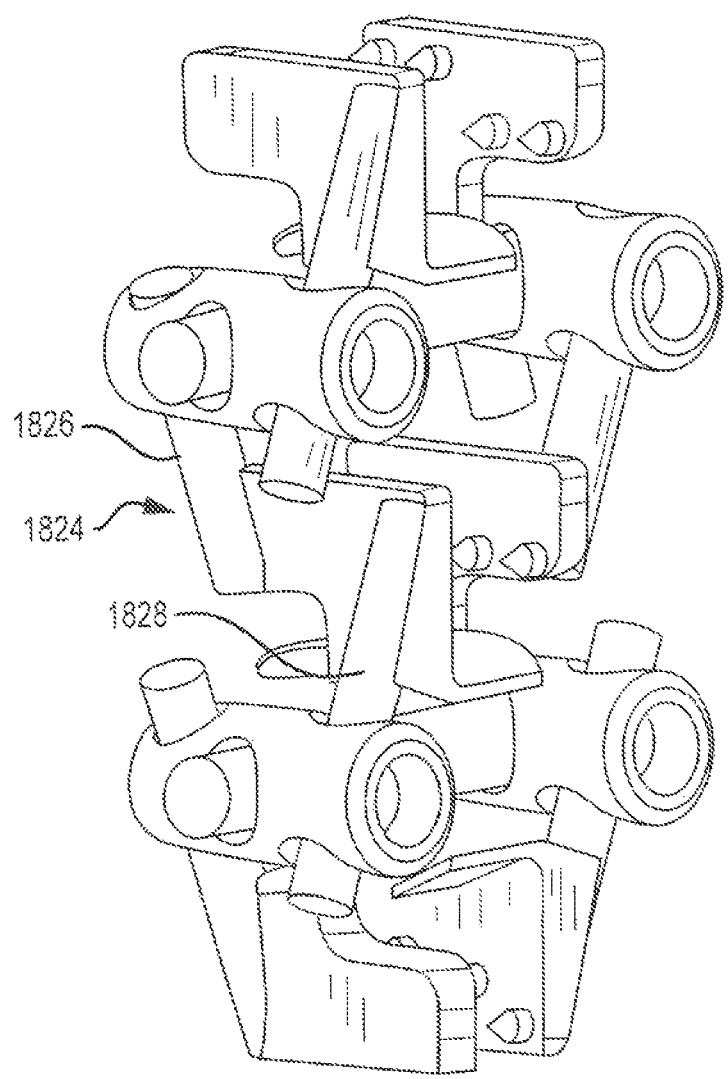

For example, in FIG. 39, a double ended extension 1824 is provided having an extension rod 1826 extending superiorly and another extension rod 1828 extending inferiorly. By using the double ended extension 1824 as a joiner, the modular implant can be assembled to treat multiple adjacent spinal levels. In the illustrative example of FIG. 39, the implant has been assembled using the double ended extension 1824 to engage three adjacent spinous processes and thus treat two adjacent spinal levels. However, any number of extensions can be assembled in this manner to treat any number of spinal levels. In addition to components, such as the double ended extension 1824, to allow treatment of multiple levels, component may be provided that are adapted to particular bone geometries. For example, extensions having flared spiked pads, extra long spikes, and screw receiving holes similar to the examples of FIGS. 31-36 may be provided, for example, to permit assembly of an implant with an inferior portion suitable for gripping a vertebra with a small or missing spinous process, such as, for example, the sacrum.

Figure 40:
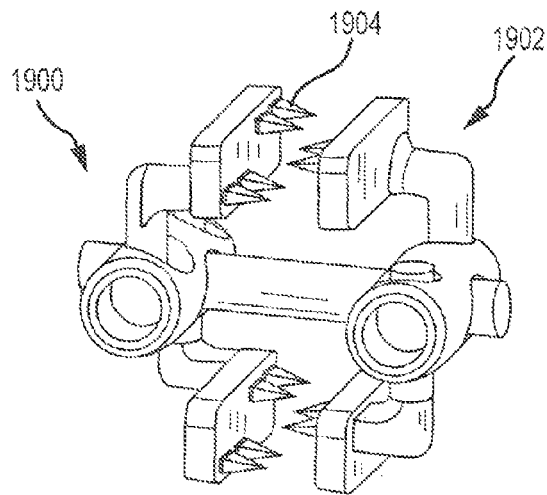

Referring to FIG. 40, an implant 1900 similar to that of FIGS. 37-39 is illustrated. The implant 1900 includes extensions 1902 having flattened spikes 1904.

Figure 41:
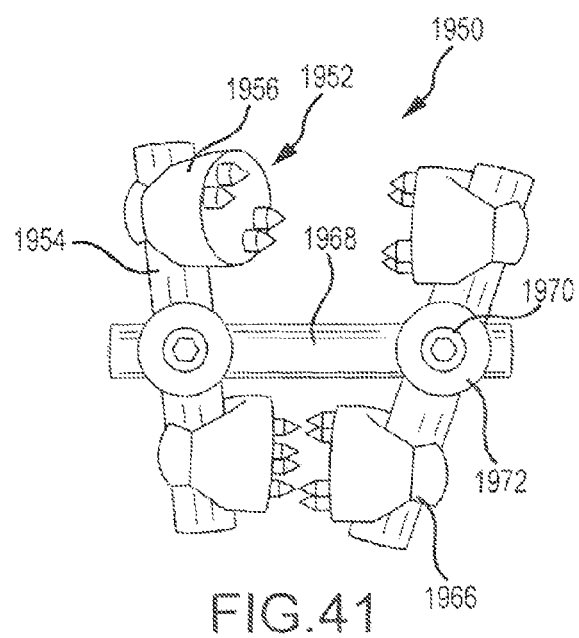
Figure 42:
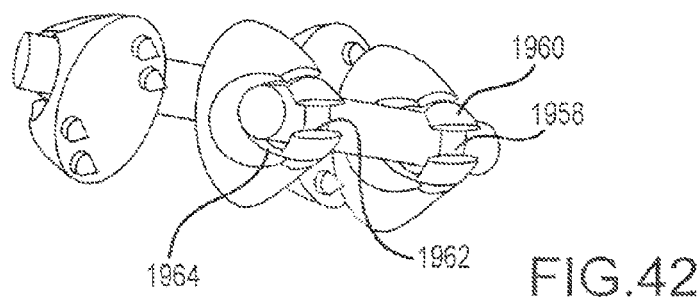
Figure 43:
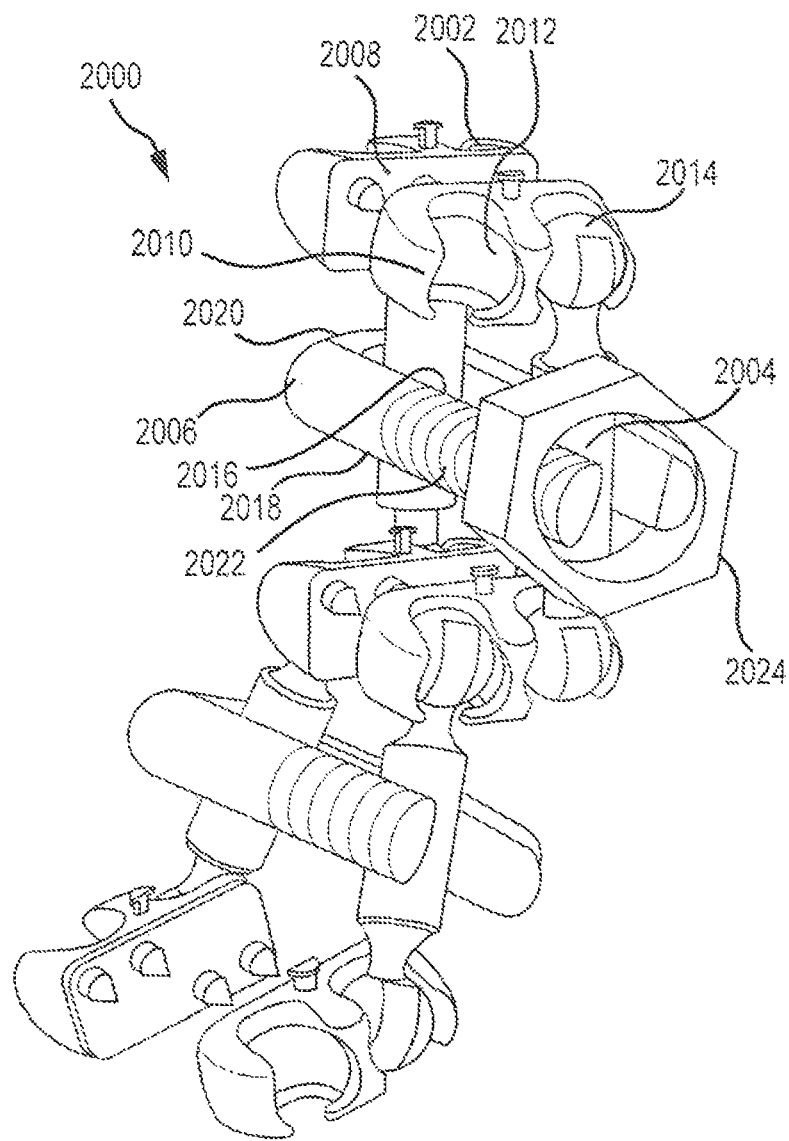

Referring to FIGS. 41-42, an implant 1950 similar to those of FIGS. 37-40 is illustrated. However, in the illustrative example of FIGS. 41-42, the extension 1952 includes an extension rod 1954 and spiked pads 1956 mounted for translation and rotation along the extension rod 1954. Each spiked pad 1956 is mounted to an extension rod 1954 with a cross drilled sphere 1958 and a split yoke 1960. The cross drilled sphere 1958 is slipped over an end of the extension rod 1954 and a first end of the split yoke 1960 is snapped over the cross-drilled sphere 1958 so that the cross-drilled sphere 1958 rides in a groove 1962 inside the split yoke 1960. A second end of the split yoke 1960 is mounted in a bore 1964 in the spiked pad 1956. The outer surface of the split yoke 1960 includes a tapered portion 1966 adjacent the mounting of the split yoke 1960 in the bore 1964. The extension rod 1954 is mounted to the cross bar 1968 with joint cylinders 1970 similar to those of the examples of FIGS. 37-40. When the joint cylinders 1970 are slid medially to engage the spiked pads 1956 with the spinous processes, each spiked pad 1956 is pressed outwardly toward the extension rod 1954. The edges of the bore 1964 slide against the tapered surface 1966 and squeeze the split yoke 1960 closed so that it is compressed around the cross-drilled sphere 1958 and extension rod 1954 and locks the relative position of the spiked pad 1956 and extension rod 1954. Referring to FIG. 43, an implant 2000 includes spiked pads 2002, extension rods 2004, and cross bars 2006. Each spiked pad 2002 has a spiked face 2008 and an opposite side 2010 having a least one spherical socket 2012 formed in it. In the illustrative example of FIG. 43, each spiked pad 2002 has two spherical sockets 2012 to permit multi-level constructs as described below. Each extension rod 2004 includes a spherical ball end 2014 formed at each of its ends. The cross bar 2006 includes a longitudinal slot 2016 dividing the cross bar 2006 into two cantilevered beams 2018 joined at a first end 2020 and threaded at a second aid 2022 for receiving a retaining nut 2024. The implant 2000 is assembled by snapping a spiked pad 2002 onto each end of each of two extension rods 2004 and placing the extension rods 2004 in the slot of the cross bar 2006. The nut 2024 is threaded onto the end of the extension rod and threadingly advanced to move the extension rods 2004 closer together and compress the spiked pads against the spinous processes. Additional spinal levels may be accommodated by snapping additional extension rods into the second holes of spiked pads, snapping additional spiked pads 2002 to the free end of the additional rods and compressing the additional assembly with an additional cross bar and nut as shown in FIG. 43.

Figure 44:
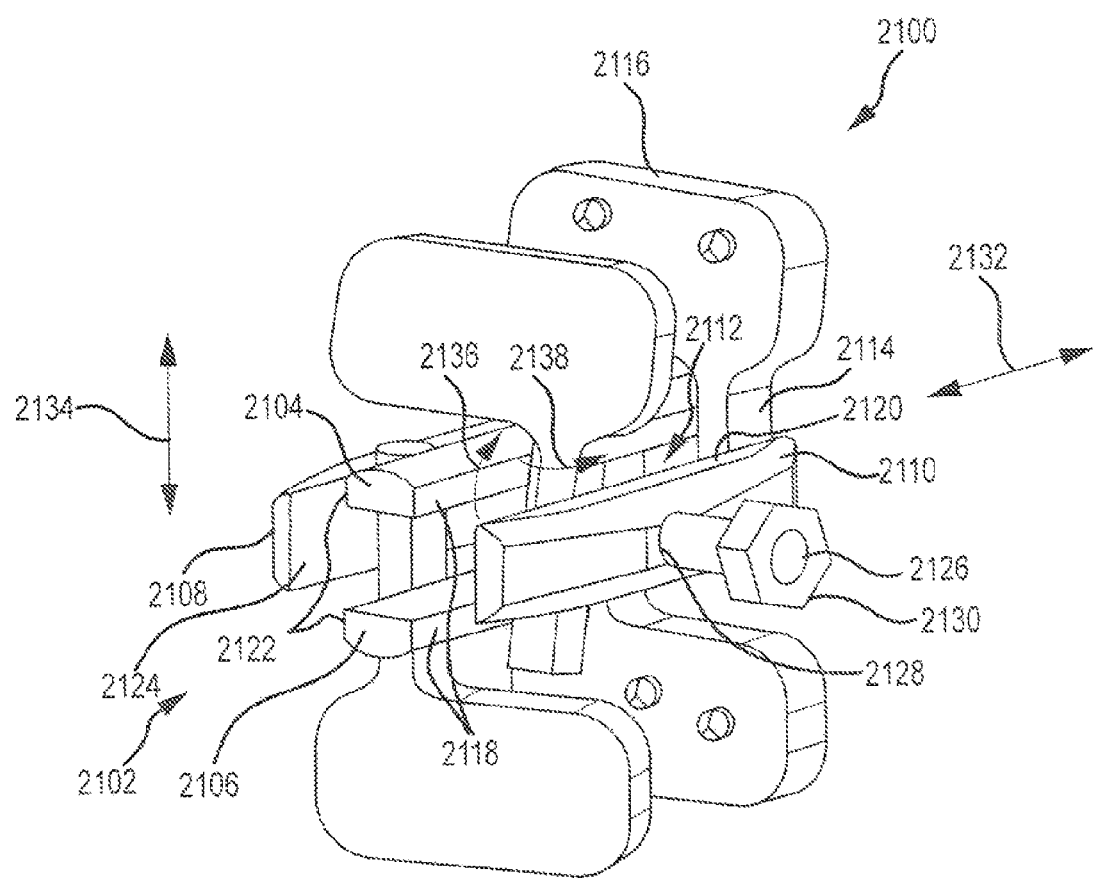

Referring to FIG. 44, an implant 2100 includes a spacer 2102 including a superior bar 2104, and inferior bar 2106, and anterior bar 2108, and a posterior bar 2110. Gaps 2112, or fenestrations, between the bars permit tissue growth between the bars and receive extension rods 2114 extending from spiked pads 2116. In the illustrative example of FIG. 44, four independent spiked pads 2116 are provided. Two of the spiked pads 2116 are supported by insertion of their extension rods 2114 between posterior surfaces 2118 of the superior and inferior bars and an anterior surface 2120 of the posterior bar. Two of the spike pads 2116 are supported by insertion of their extension rods 2134 between anterior surfaces 2122 of the superior and inferior bars and a posterior surface 2124 of the anterior bar. A bolt 2126 extends from the anterior bar 2108 through a bore 2128 in the posterior bar 2110 and is secured with a nut 2130. Tightening the nut 2130 compresses the bars and extension posts together to lock the position of the spiked pads 2136. Loosening the nut 2130 allows independent adjustment of each spiked pad 2116 medially-laterally 2132, superiorly-inferiorly 2134, angularly 2136, and rotationally 2138.

Figure 45:
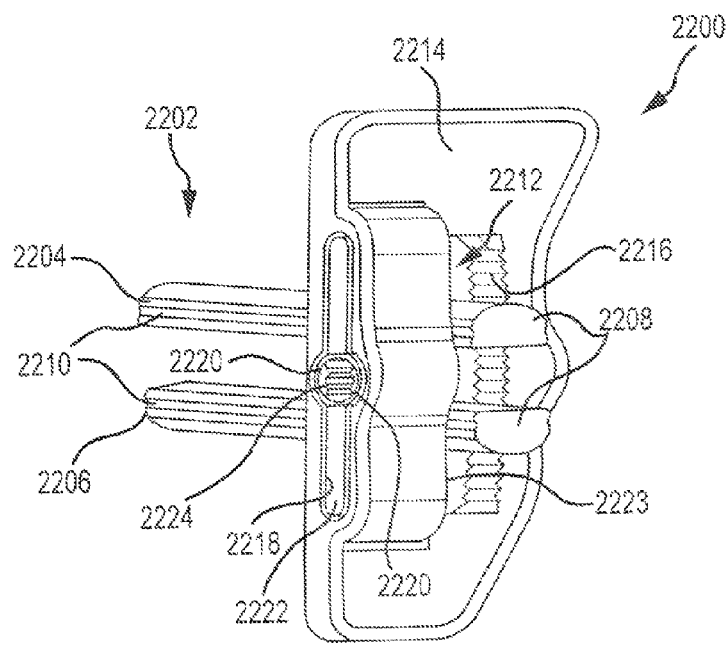
Figure 46:
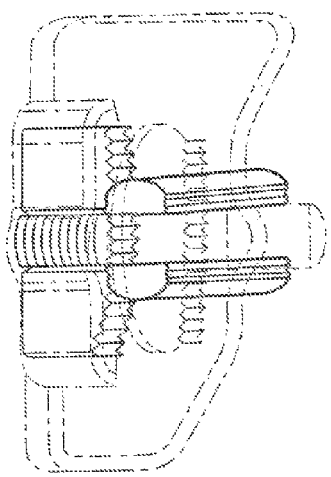
Figure 47:
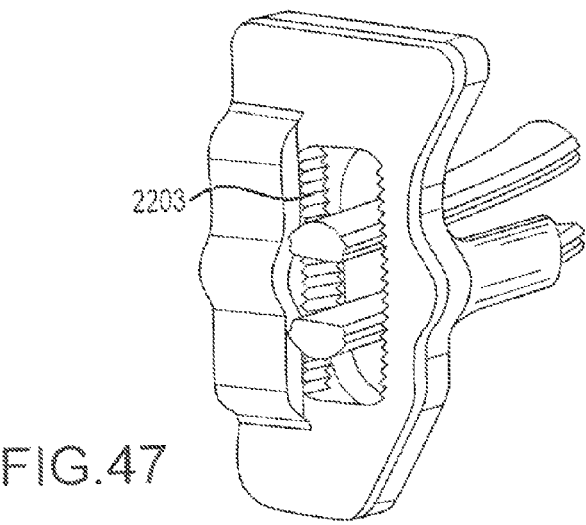

Referring to FIGS. 45-47, a portion of an implant 2200 is shown to illustrate a mechanism tor providing an adjustable height spacer 2202 having a superior bar 2204 and an inferior bar 2206. The 2204, 2206 bars include longitudinal serrations on their anterior sides 2208 and posterior sides 2210. The bars 2204, 2206 are received in a first superiorly-inferiorly elongated slot 2212 formed in an extension 2214. The first slot 2212 includes anterior serrations 2216 engageable with the anterior serrations 2208 of the bars 2204, 2206 to support the bars in a selected superior-inferior position. A second superiorly-inferiorly elongated slot 2218 is formed in the extension 2214 transverse to the first slot 2212. The second slot 2218 includes opposed hemi-cylindrical threaded concavities 2220 formed in its sidewalls and directed toward the first slot 2212. The second slot 2218 receives a lock block 2222 in sliding relationship toward the first slot 2212 and the threaded concavities 2220 receive a lock screw 2224 in threaded relationship. The lock block 2222 includes anterior facing serrations 2223 engageable with the posterior serrations 2210 of the bars 2204, 2206. In use, the bars 2204, 2206 and extension 2214 are engaged with the bars 2204, 2206 received in the first slot 2212. The bars 2204, 2206 are adjusted superiorly-inferiorly and medially-laterally within the first slot 2212 to a desired position relative to the extension 2214. The lock screw 2224 is then rotated causing the lock screw to advance toward the first slot 2212 and drive the lock block 2222 toward the first slot 2212. The lock block 2222 presses against the bars 2204, 2206 causing the serrations of the lock block 2222, bars 2204 and 2206, and first slot 2212 to engage and Sock the desired relative position between the extension 2214 and rods 2204, 2206. Alternatively, the serrations may be omitted and locking accomplished by frictional engagement.

The mechanism of FIG. 44 may be substituted in the preceding examples. For example the mechanism of FIG. 44 may be substituted in the implant 100 of FIGS. 1-9 to provide implant 100 with an adjustable height spacer.

Figure 48:
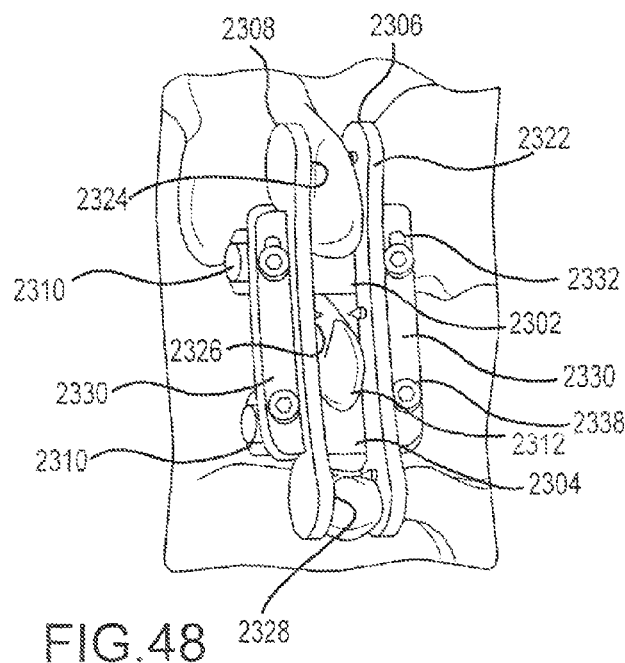
Figure 49:
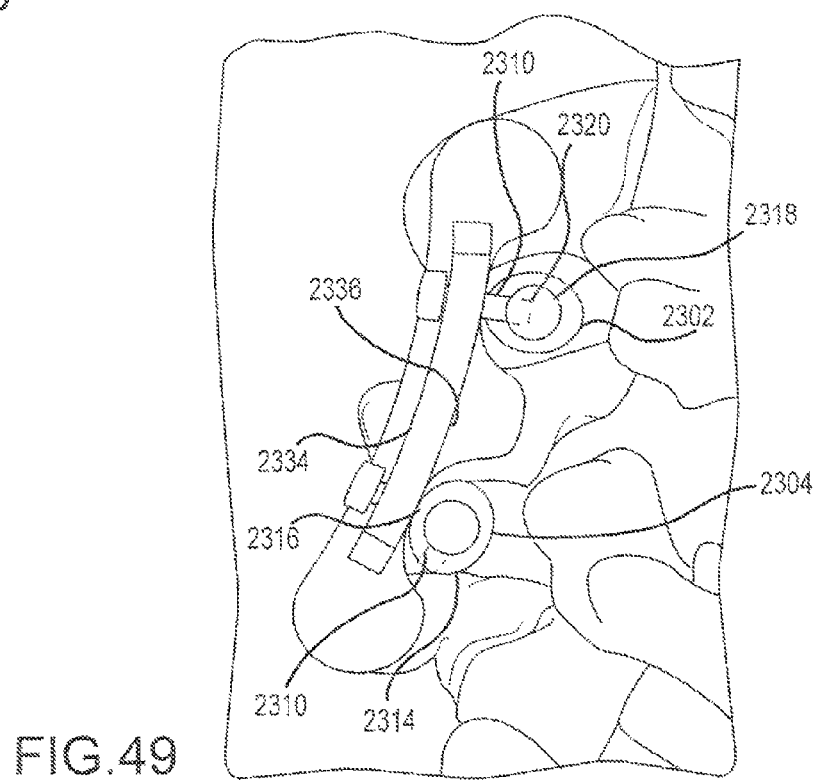

Referring to FIGS. 48-49, an implant 2300 suitable for treating multiple spinal levels includes multiple spacers 2302, 2304 and first and second unitary, multilevel extensions 2306. Each spacer includes an elongated, hollow, body having a non-circular cross-sectional shape (FIG. 49). Each spacer further includes at each end a first slot 2310 formed through its sidewall and extending a short distance longitudinally toward the opposite end of the spacer to an inboard end of the first slot. Each spacer further includes a second slot (not shown) formed through its sidewall and extending circumferentially from the inboard end of each first slot 2310 to a third slot 2312. In the illustrative example of FIGS. 48-49, the first slot 2310 is formed in a relatively narrow side 2314 of the non-circular spacer and the third slot 2312 is formed in a relatively wide side 2316 of the non-circular spacer, the sides being approximately ninety degrees apart (FIG. 49). A cylindrical nut 2318 is provided to fit inside the hollow body at each end of each spacer 2302. The nut 2318 includes a threaded cross-bore 2320. The extensions 2306 each include a generally flat, medially facing surface 2322 having multiple spiked regions 2324, 2326, 2328 and a flange 2330 extending laterally from the extension 2306. Each flange 2330 includes superiorly-inferiorly elongated holes 2332 extending through the flange 2330 from a posterior surface 2334 to an anterior surface 2336. Lock bolts 2338 are provided to join the extensions 2306 to the spacers 2302, 2304. In use, the lock bolts 2338 are extended through the flanges 2330 and a nut 2318 is loosely threaded onto each bolt. The spacers 2302, 2304 are placed between adjacent spinous processes initially with their narrow dimension opposing the spinous processes as shown with the superior spacer 2302 in FIG. 49. The extensions 2306 are positioned on opposite sides of the spinous processes and the nuts 2318 are slipped into the hollow interior of the spacers with the bolts 2338 sliding through the first slot as shown with the superior spacer 2302 in FIG. 49. The elongated holes 2332 in the flanges 2330 permits superior-inferior adjustment of the spacers 2302, 2304 relative to the extensions 2306. The spacers 2302, 2304 are then rotated to position their wide dimension opposing the spinous processes as shown with the inferior spacer 2304 in FIG. 49. This rotation may be accomplished for example by engaging an instrument with the first slit to apply a torque to the spacer. Rotation of the spacers 2302, 2304 causes the spinous processes to move apart as the wide dimension of the spacers is rotated between the spinous processes. As the spacers rotate, the bolts 2338 slide through the second slot (not shown) until they are aligned with the third slot 2312 in the spacer. The extensions 2306 are now compressed medially to engage the spikes with the spinous processes. The bolts 2338 slide within the third slot 2312 during compression. Once the bolts move inward of the second slots, the spacers are prevented from rotating back by the bolts 2338 abutting the sides of the third slot 2312. The bolts 2338 are tightened to lock the position of the spacers 2302, 2304 relative to the extensions 2306.

While a specific illustrative example and use of implant 2300 has been shown and described, it is to be understood that implant 2300 can be assembled in any order. For example, the nuts 2318 may first be slipped into the spacers 2302, 2304, the spacers placed between the spinous processes in a desired final position, the extensions 2306 compressed medially into the spinous processes, and then the bolts 2338 inserted and tightened. Likewise, while implant 2300 has been shown to treat two spinal levels, it can be readily modified to treat one, three, four, five or any number of spinal levels. Likewise, while the spacers 2302, 2304 have been shown with two different dimensions and being rotated to facilitate distraction of the spinous processes, the spacers 2302, 2304 may be inserted without rotation and may have, for example, a single slot for receiving bolts 2338.

Figure 50:
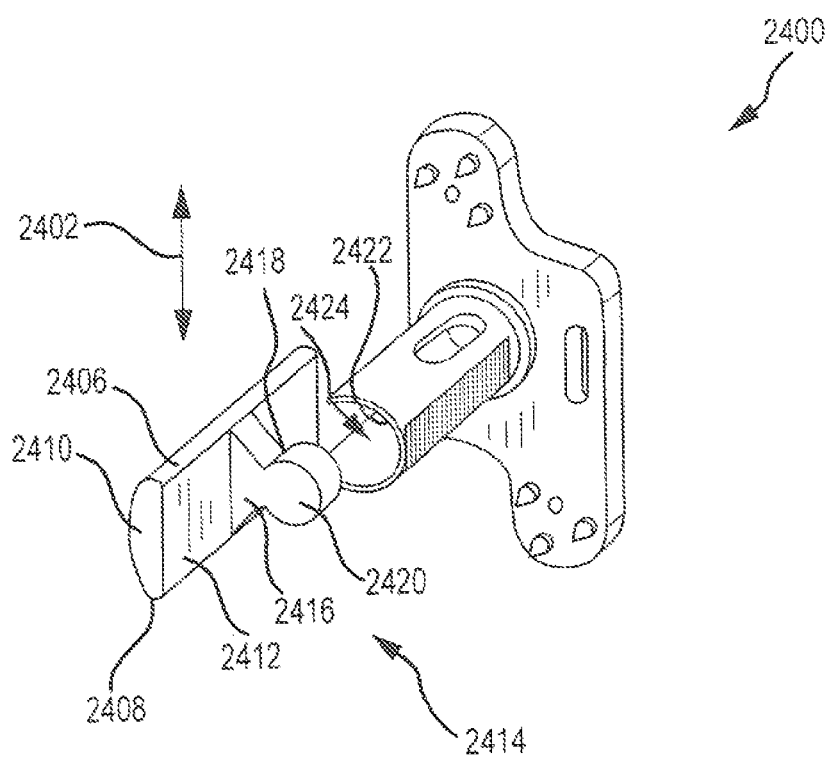
Figure 51:
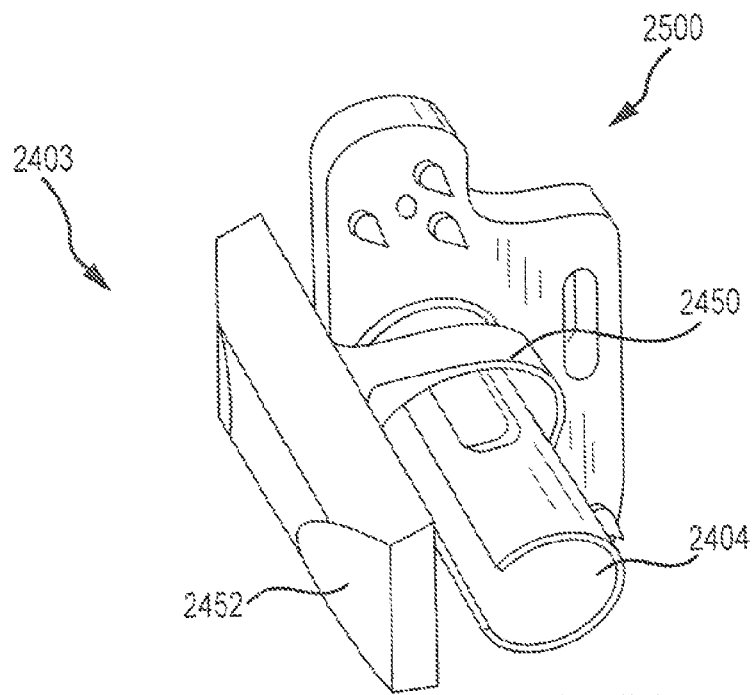

Referring to FIGS. 50-51, an implant 2400, similar to that of FIGS. 1-9, further includes a separate member 2402, 2403 engageable with the spacer 2404 to be positioned between adjacent vertebrae. The separate member 2402, 2403 may be used to provide additional structural support, to provide bone growth promoting material or both. The member 2402, 2403 may be made of metal, plastic, bone, ceramic, or any other suitable material. For example, the member 2402, 2403 may be a structural bone graft that both contributes to the support of the spacing between adjacent vertebrae and provides bone growth promoting minerals and scaffolding to the surgical site. Also, for example, the member 2402, 2403 may be coupled to the spacer to provide additional material anterior of the spacer. The member 2402, 2403 may be sized smaller (superiorly-inferiorly) than the spacer 2404 so that it bears little, if any of the load of adjacent vertebrae. Or, the member 2402, 2403 may be sized similarly to the spacer 2404 so that it shares the load of adjacent vertebrae. Or, the member 2402, 2403 may be sized larger than the spacer 2404 so that it bears most, or all, of the load of adjacent vertebrae. For example, the member 2402, 2403 may be a structural allograft bone member that is sized slightly larger than the spacer 2404 to bear the load of adjacent vertebrae to encourage bone growth. However, if the member 2402, 2403 were to resorb or subside, the adjacent vertebrae would then be safely supported by the spacer 2404. Referring to FIG. 50, the member 2402 is generally in the form of a plate-like body having a superior surface 2406, an inferior surface 2408, a convex anterior surface 2410, and generally flat posterior surface 2412 and a posteriorly projecting connecting member 2414. The connecting member includes a base 2416 joined to the posterior surface 2412 tapering to a neck 2418 connected to an expanded engagement end 2420. The engagement end 2420 has a cross-sectional shape corresponding to the cross sectional shape of the interior 2422 of the spacer 2404. In use, the member 2402 is coupled to the spacer 2404 by sliding the engagement end 2420 into the interior 2422 of the spacer 2404 with the neck 2438 sliding within an anteriorly opening slot 2424 of the spacer 2404. While the member 2402 is shown in use to augment the anterior side of the spacer 2404, it may be configured to augment any one or multiple sides of the spacer 2404.

Referring to FIG. 51, the member 2403 is similar to member 2402 of FIG. 50 except that instead of engaging the interior of the spacer 2404 it engages the exterior of the spacer 2404 with a ring-shaped engagement member 2450 that slides over the spacer 2404. In addition, the member 2403 includes chamfers 2452 at each end to provide clearance for portions of the vertebrae such as, for example, the facet joints.

Figure 52:
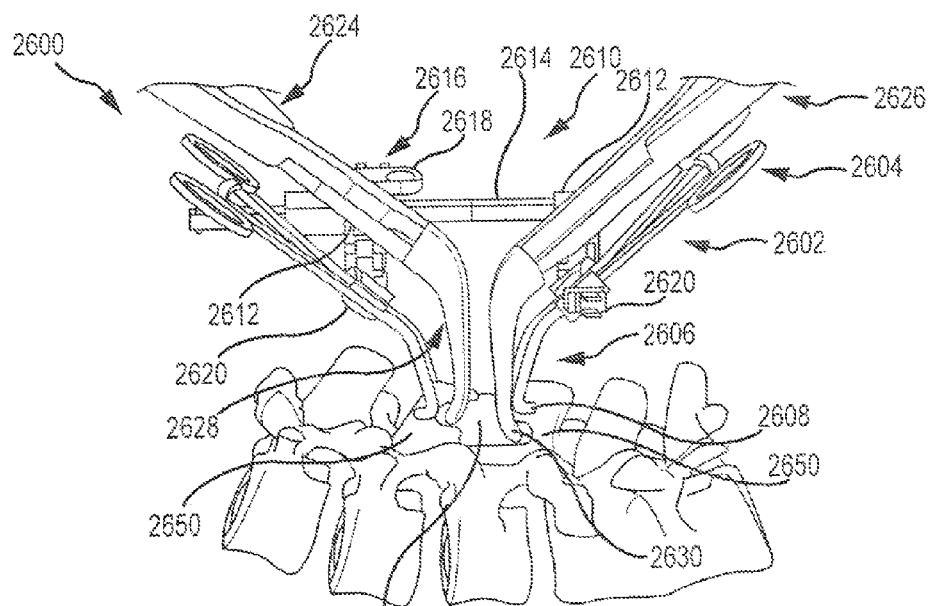
Figure 53:
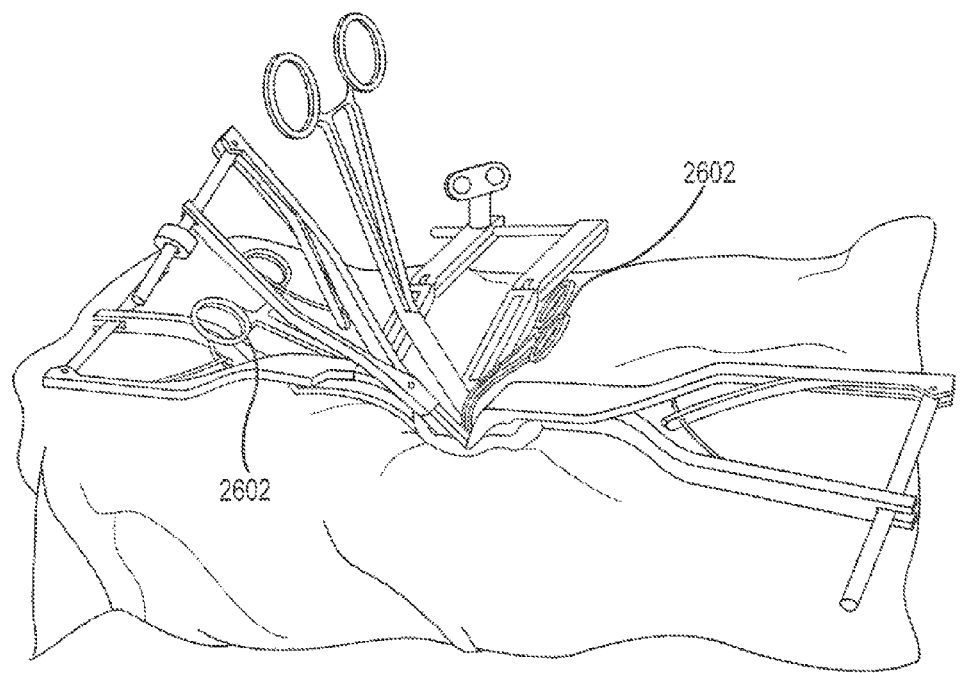

Referring to FIGS. 52-53, a set 2600 of instruments for distracting or compressing adjacent vertebrae away from or toward one another and for compressing implant extensions medially toward the spinous processes is illustrated. The set 2600 includes a pair of Kocher-style bone clamps 2602 having a scissor-like action with a handle end 2604 and a working end 2606 terminating in bone gripping lips 2608. A Caspar-style compressor/distracter 2610 includes arms 2612 joined by a rack 2614 extending from one arm and engaging a gear assembly 2616 mounted on another arm. A knob 2618 is responsive to rotation to rotate a pinion (not shown) relative to the rack 2614 and cause the rack to translate. Rotation of the knob 2618 in a first direction causes the arms 2612 to move away from one another and rotation of the knob 2618 in an opposite direction causes the arms 2612 to move toward one another. The arms 2612 terminate in arm clamps 2620 able to receive the Kocher-style bone clamps 2602. The set 2600 further includes implant compressors 2624 having a scissor-like action with a handle end 2626 and a working end 2628 terminating in implant gripping tips 2630.

In use, an implant 100 is positioned with spacer between adjacent spinous processes 2650 and extensions on each side of the spinous processes 2650. The bone clamps 2602 are clamped to the vertebrae. For example, they are clamped to adjacent spinous processes 2650. The arm clamps 2620 of the compressor/distracter are attached to the bone clamps 2602. The knob 2618 is then rotated to compress or distract the arms 2612, and by extension the bone clamps 2602, until the vertebrae are in a desired relative spacing. The implant compressors 2624 are then engaged with the implant 100 and compressed to cause the extensions of the implant to engage the spinous processes to secure the desired spacing between the vertebrae.

Figure 54:
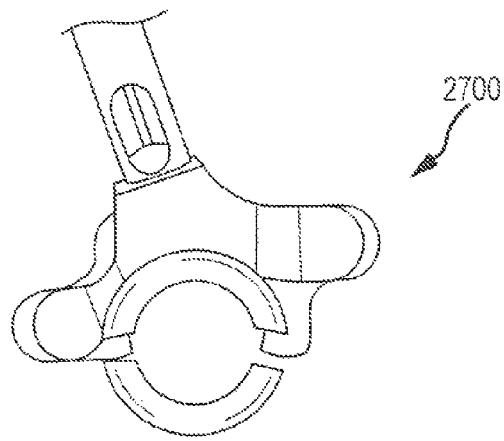
Figure 55:
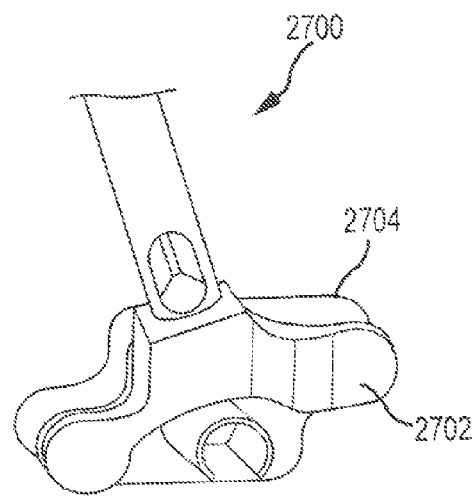
Figure 56:
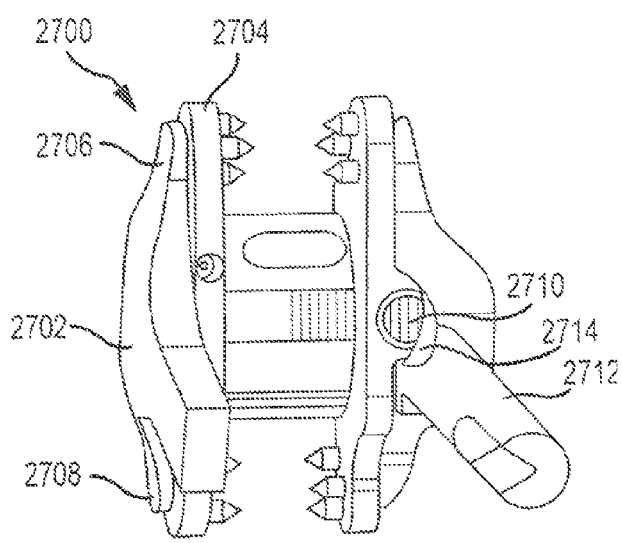

Referring to FIGS. 54-56, an alternative tip configuration 2700 for the implant compressor 2624 of FIGS. 52-53 is illustrated. The tips 2700 include extensions 2702 having a profile contoured to generally match the posterior profile of the implant extensions 2704 to distribute compressive forces over the surface of the implant extensions 2704. The compressor extensions 2702 taper toward their superior and inferior aspects 2706, 2708 to minimize the space needed superiorly and inferiorly for tip insertion and to decrease the amount of the surgical view that is obstructed by the tips. Where the implant includes a set screw bore 2710, the extension 2702 and arm 2710 may include a relieved portion 2712 aligned with the set screw bore 2710 to permit driving a set screw in the bore 2710.

Figure 57:
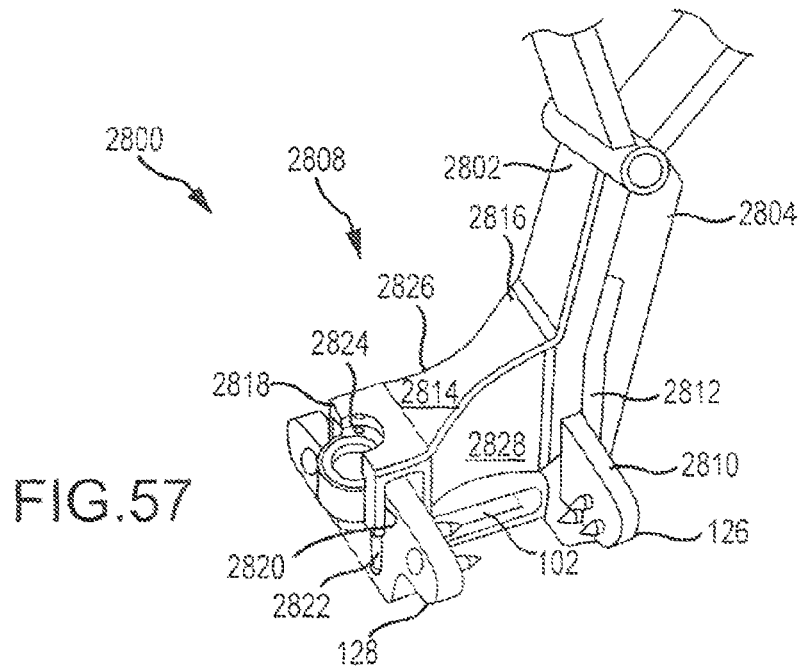

Referring to FIG. 57, an implant inserter 2800 is useful for inserting an implant 100 similar to that of FIGS. 1-9 in a direct posterior approach. The inserter 2800 includes a first arm 2802 and a second arm 2804 joined in a scissor-like arrangement and having a handle 2806 end and a working end 2808. The working end of each arm 2802, 2804 includes a clamping face 2810, 2812 movable toward and away from one another in response to movement of the working end of the arms toward and away from one another. The clamping faces 2810, 2812 are operable to clamp, and thereby grip, the first extension 126 of the implant 100. The first arm 2802 includes a foot 2814 projecting medially from first end 2816 near the clamping faces 2810, 2812 to a second end 2838 spaced from the clamping faces 2810, 2812. The foot 2814 is positionable over the spacer 102 when the clamping faces 2810, 2812 are in clamping engagement with the first extension 126. A slot 2820 is formed near the second end 2818 of the foot 2814 and extends posteriorly from an anterior edge 2822 of the foot 2834. The slot 2820 is sized to receive the second extension 128.

In use, the second extension 128 is placed on the spacer 102 and the inserter 2800 is engaged with the implant by positioning the foot over the spacer 102 such that the slot 2820 receives the second extension 128 and the clamping faces 2810, 2812 are on opposite sides of the first extension 126. The inserter handles 2806 are operated to clamp the first extension 126. Thus clamped, the first and second extensions 126, 128 are held securely in a predetermined spaced relationship. If desired, the set screw 130 (FIG. 3) may be inserted and tightened to further secure the second extension 128 in anticipation of eventual removal of the inserter 2800. A relief cut 2824 through the foot 2814 posteriorly-to-anteriorly is aligned with the set screw bore to facilitate operation of the set screw while the implant 100 is engaged with the inserter. The inserter 2800 may be used to insert the implant 100 in a direct posterior-to-anterior direction between adjacent spinous processes. The superior and inferior aspects 2826, 2828 of the foot 2814 may be relieved to avoid tissue impingement on the foot 2814 and to improve visualization.

Figure 58:
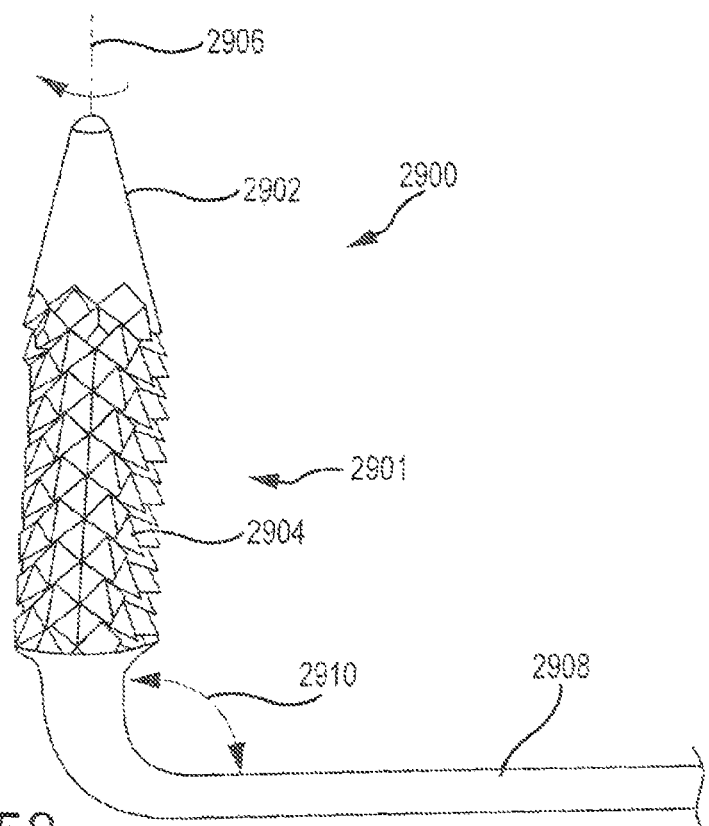

Referring to FIG. 58, a rasp 2900 is provided for rasping adjacent tissues, for example, for removing tissue between adjacent spinous processes in preparation for insertion of the implant 100. The rasp 2900 includes head 2901 having a conical tip 2902 to aid insertion and teeth 2904. Insertion and removal of the rasp head 2901 along its longitudinal axis and rotation of the rasp head 2901 about its longitudinal axis 2906 will remove abutting tissue. In the case of its use to prepare adjacent spinous processes, an angled handle 2908, for example forming an angle 2910 in the range of 135 to 45 degrees, more preferably in the range of 120 to 60 degrees, more preferably at about 90 degrees, is useful to position the head 2901 between the spinous processes and rotate it back and forth about its axis to abrade tissue. The teeth 2904 are angled toward the handle 2908 to ease the initial insertion of the head 2901. The angled teeth 2904 are less prone to snagging upon insertion.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

What is claimed is:

1. An implant for placement between spinous processes of adjacent vertebrae of a spine, the implant comprising:
  a spacer including a first end, a second end, and a longitudinal axis extending from the first end to the second end, the spacer including a superior bar and an inferior bar each aligned with the longitudinal axis and including a posterior surface and an anterior surface;
  a first extension coupled to a first end of the spacer, the implant including a locking mechanism adapted to secure the first extension in a first position relative to the superior bar and the inferior bar; and
  a second extension opposing the first extension and slidably coupled to the spacer along the superior bar and the inferior bar between the first extension and the second end of the spacer, the locking mechanism adapted to secure the second extension in a second position relative to the superior bar and the inferior bar;
  wherein engagement of the locking mechanism on the first extension and the second extension determines an adjustable spacing between the first extension and the second extension along a superior-inferior axis, wherein the locking mechanism includes an anterior bar and a posterior bar.

2. The implant of claim 1 wherein the locking mechanism includes a bolt connecting the anterior bar and the posterior bar and a nut threaded on the bolt to tighten the locking mechanism.

3. The implant of claim 1, wherein each of the first extension and the second extension include extension rods extending between the anterior bar and the posterior bar of the locking mechanism.

4. The implant of claim 1, wherein each of the first extension and the second extension include a superior spiked pad or an inferior spiked pad.

5. The implant of claim 4, wherein the superior spiked pad moves separately from the inferior spiked pad along both the longitudinal axis and the superior-inferior axis.

6. The implant of claim 4, wherein the superior spiked pad and the inferior spiked pad are independently adjustable in a medial-lateral direction, in angulation relative to the longitudinal axis, and in rotation relative to the longitudinal axis.

7. The implant of claim 4, wherein the posterior bar extends along at least a portion of the longitudinal axis and the anterior bar extends along the portion of the longitudinal axis opposite the posterior bar.

8. The implant of claim 7, wherein the posterior bar and the anterior bar are coupled by a bolt and secured with a nut to fix the first extension and the second extension in the first position and second position respectively.

9. An interspinous implant comprising:
  a superior bar extending along a longitudinal axis of the implant;
  an inferior bar extending along the longitudinal axis;
  a first extension including a first extension rod running transverse to the longitudinal axis in a superior-inferior direction and in a first position along a posterior side the superior bar and the inferior bar;
  a second extension coupled in a second position along an anterior side of the superior bar and the inferior bar and opposing the first extension, the second extension including a second extension rod to secure the second extension; and
  a locking mechanism including an anterior bar and a posterior bar capturing the first extension and the second extension against the superior bar and the inferior bar;
  wherein positioning of the first extension rod and the second extension rod determine an adjustable spacing between the first extension and the superior bar and the second extension and the inferior bar along a transverse axis.

10. The implant of claim 9, wherein the locking mechanism includes a bolt and nut arrangement to secure the anterior bar and the posterior bar against the superior bar and the inferior bar.

11. The implant of claim 9, wherein the first extension includes a first spiked pad coupled to a superior end of the first extension rod.

12. The implant of claim 11, wherein the second extension includes a second spiked pad coupled to an inferior end of the second extension opposite the first spiked pad.

13. The implant of claim 9, wherein the first spiked pad and the second spiked pad are independently adjustable in a medial-lateral direction, in angulation relative to the longitudinal axis, and in rotation relative to the longitudinal axis.

14. An interspinous implant comprising:
a superior bar extending along a longitudinal axis of the implant;
an inferior bar extending along the longitudinal axis;
a first extension engaging first ends of the superior bar and the inferior bar, the implant including a locking mechanism adapted to secure the first extension in a first position relative to the superior bar and the inferior bar; and
a second extension opposing the first extension and slidably engaging the superior bar and the inferior bar between the first extension and second ends of the superior bar and the inferior bar, the locking mechanism adapted to secure the second extension in a second position relative to the superior bar and the inferior bar; wherein the first position of the first extension and the second position of the second extension determine the adjustable spacing between a superior portion of the first extension and an inferior portion of the second extension along superior-inferior axis,
wherein the locking mechanism includes:
an anterior bar positioned on an anterior side of the superior bar and the inferior bar;
a posterior bar positioned on a posterior side of the superior bar and the inferior bar; a bolt coupling the anterior bar to the posterior bar; and
a nut threadable onto the bolt to secure first extension and the second extension determining the adjustable spacing between the superior portion of the first extension and inferior portion of the second extension.

15. The implant of claim 14, wherein the superior portion of the first extension includes a first superior spiked pad for interfacing with a first vertebrae; and
wherein the inferior portion of the second extension includes a second inferior spiked pad for interfacing with a second vertebrae.

16. The implant of claim 15, further comprising:
a third extension positioned longitudinally opposite the first extension, the third extension including a second superior spiked pad for interfacing with the first vertebrae; and
a fourth extension positioned longitudinally opposite the second extension, the fourth extension including a second inferior spiked pad for interface with the second vertebrae.

17. The implant of claim 16, wherein the first superior spiked pad, the first inferior spiked pad, the second superior spiked pad, and the second inferior spiked pad are individually positionable along the longitudinal axis of the implant;
wherein the first superior spiked pad and the first inferior spiked pad abut a medial side of the first vertebrae and the second vertebrae respectively; and
wherein the second superior spiked pad and the second inferior spiked pad abut a lateral side of the first vertebrae and the second vertebrae respectively.

\* \* \* \* \*